US009468627B2

(12) United States Patent
Jacobsen et al.

(10) Patent No.: US 9,468,627 B2
(45) Date of Patent: Oct. 18, 2016

(54) SLOW-RELEASE FORMULATIONS OF 5-HYDROXYTRYPTOPHAN AS AN ADJUNCT TO PRO-SEROTONERGIC THERAPIES

(71) Applicant: Duke University, Durham, NC (US)

(72) Inventors: Jacob P. R. Jacobsen, Durham, NC (US); Marc G. Caron, Hillsborough, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/866,145

(22) Filed: Apr. 19, 2013

(65) Prior Publication Data

US 2013/0230577 A1    Sep. 5, 2013

Related U.S. Application Data

(63) Continuation of application No. PCT/US2011/057247, filed on Oct. 21, 2011.

(60) Provisional application No. 61/405,831, filed on Oct. 22, 2010, provisional application No. 61/504,354, filed on Jul. 5, 2011.

(51) Int. Cl.

| | | |
|---|---|---|
| *A61K 31/405* | (2006.01) | |
| *A61K 31/137* | (2006.01) | |
| *A61K 9/70* | (2006.01) | |
| *A61K 45/06* | (2006.01) | |
| *A61K 31/138* | (2006.01) | |
| *A61K 31/343* | (2006.01) | |

(52) U.S. Cl.
CPC ........... *A61K 31/405* (2013.01); *A61K 9/7023* (2013.01); *A61K 31/137* (2013.01); *A61K 31/138* (2013.01); *A61K 31/343* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,958,447 A | 9/1999 | Haralambopoulos et al. | |
| 6,818,229 B1 | 11/2004 | Cefali et al. | |
| 7,517,908 B2 * | 4/2009 | Krishnan et al. | 514/469 |
| 7,585,627 B2 | 9/2009 | Caron et al. | |
| 7,645,766 B1 * | 1/2010 | Delack | A61K 31/40 424/400 |
| 8,377,474 B2 | 2/2013 | Hsu et al. | |
| 2006/0013876 A1 * | 1/2006 | Lohray | A61K 9/0065 424/472 |
| 2006/0045913 A1 | 3/2006 | Mihaylov | |
| 2006/0094765 A1 | 5/2006 | Coelingh Bennink et al. | |
| 2007/0117844 A1 | 5/2007 | Morillo et al. | |
| 2007/0213370 A1 * | 9/2007 | Sanchez Morillo | A61K 31/137 514/317 |
| 2007/0292493 A1 | 12/2007 | Brierre | |
| 2009/0192166 A1 | 7/2009 | Krishnan et al. | |
| 2010/0055133 A1 * | 3/2010 | Duffield | A61K 9/2054 424/239.1 |
| 2010/0256116 A1 | 10/2010 | Caron et al. | |
| 2010/0298379 A1 | 11/2010 | Jacobsen | |

FOREIGN PATENT DOCUMENTS

| | | | |
|---|---|---|---|
| EP | 1 637 185 A1 | | 3/2006 |
| WO | WO 2005/112906 | * | 1/2005 |
| WO | WO 2005/112906 A2 | | 12/2005 |
| WO | WO 2009/042632 A2 | | 4/2009 |
| WO | WO 2009/043834 | * | 4/2009 |
| WO | WO 2009/043834 A1 | | 4/2009 |
| WO | WO 2011/077406 A2 | | 6/2011 |
| WO | WO 2012/054815 A1 | | 4/2012 |

OTHER PUBLICATIONS

International Search Report and Written Opinion, PCT/US2011/057247, mailed Feb. 28, 2012.
5HTP: MedlinePlus Supplements. U.S. National Library of Medication, NIH National Institutes of Health. http://www.nlm.nih.gov/medlineplus/druginfo/natural/794.html. 4 pages, retrieved Aug. 25, 2012.
Alino; Jjl-I et al. "5-hydroxytryptophan (5-HTP) and a MAOI (nialamide)in the treatment of depressions" Int. Pharmacophychiat. 1976; 11: 8-15.
Grabowski et al. "Fluoxetine Is Ineffective for Treatment of Cocaine Dependence or Concurrent Opiate and Cocaine Dependence: Two Placebo-Controlled, Double-Blind Trials" Journal of Clinical Psychopharmacology, 1995, vol. 15, pp. 163-174.
Jacob P R Jacobsen et al. "Insensitivity of NMRI mice to selective serotonin reuptake inhibitors in the tail suspension test can be reversed by co-treatment with 5-hydroxytryptophan", Psychopharmacology, Springer, Berlin, DE, vol. 199, No. 2, May 22, 2008, pp. 137-150.
Livestrong.com. "Can you take SSRIs and 5-HTP together?" www.livestrong.com/article/455433-can-you-take-ssris-5-htp-together. 4 pages, retrieved Jun. 27, 2013.
Livestrong.com. "How to combine 5-HTP and SSRI" www.livestrong.com/article/425239-how-to-combine-5-htp-ssri. 4 pages; retrieved Jun. 27, 2013.
Maderuelo C et al. "Critical factors in the release of drugs from sustained release hydrophilic matrices" Journal of Controlled Release. 2011; 154: 2-19.
Nardini M et al. "Treatment of depression with L-5-hydroxytryptophan combined with chorimipramine, a double-blind study" Int. J. Clin. Pharm. Res. 1983; III(4): 239-250.
Perry et al. "Extracellular 5-hydroxytryptamine concentration in rat hypothalamus after administration of fluoxetine plus L-5-hydroxytryptophan" J. Pharm. Pharmacol, 1993, vol. 45, No. 759-761.
Sanson, L. N. "Oral extended-release products", Aust Prescr, 1999, vol. 22, pp. 88-90.
Scahill et al. "Fluoxetine Has no Marked Effect on Tic Symptoms in Patients with Tourette's Syndrome: A Double-Blind Pacebo-Controlled Study", Journal of Child and Adolescent Psychopharmacology, 1997, vol. 7, No. 2,pp. 75-85.

(Continued)

*Primary Examiner* — Robert A Wax
*Assistant Examiner* — Danah Al-Awadi
(74) *Attorney, Agent, or Firm* — Myers Bigel & Sibley, P.A.

(57) ABSTRACT

The present invention concerns the treatment of serotonergic dysregulation disorders and/or augmentation of serotonin levels in the brain by add-on treatments to serotonin enhancers, and slow-release formulations of 5-hydroxytryptophan (5-HTP) therefor.

32 Claims, 11 Drawing Sheets

(56) References Cited

OTHER PUBLICATIONS

Shaw K et al. "Tryptophan and 5-hydroxytryptophan for depression" Cochrane Database Syst Rev. 2002;(1):CD003198. http://www.ncbi.nlm.nih.gov/pubmed/11869656. 2 pages, retrieved Jan. 17, 2013.
Thombre AG. "Assessment of the feasibility of oral controlled release in an exploratory development setting" Drug Discovery Today. Sep. 2005; 10(17): 1159-1166.
Turner EH et al. "Serotonin a la carte: supplementation with the serotonin precursor 5-hydroxytryptophan" Pharmacology & Therapeutics. Mar. 2006; 109: 325-338.
Van Hiele LJ. "I-5-hydroxytryptophan in depression: the first substitution therapy in psychiatry?" Neuropsychobiology. 1980; 6: 230-240.
Van Praag HM. "Serotonin precursors in the treatment of depression" Advances in Biochemical Psychopharmacology. 1982:; 34: 259-286.
Van Praag, HM et al. "5-hydroxytryptophan in combination with clomipramine in "therapy-resistant" depressions." Psychopharmacologia (Berl.).1974; 38: 267-269.
Wong et al. "Prozac (Fluoxetine, Lilly 110140), The First Selective Serotonin Uptake Inhibitor and an Antidepressant Drug: Twenty Years Since its First Publication" Life sciences, 1995, vol. 57, No. 5, pp. 411-441.
Adderall XR, FDA Package Insert, Shire US Manufacturing, Inc., pp. 1-10.
Adeyeye et al., "Development and Evaluation of Sustained-Release Ibuprofen-Wax Microspheres. II. In Vitro Dissolution Studies", Pharmaceutical Research, 1994, 11(4): 575-579.
Amrol, D., "Single-dose azithromycin microsphere formulation: a novel delivery system for antibiotics", International Journal of Nanomedicine, 2007, 2(1): 9-12.
Beaulieu et al., "Role of GSK3β in behavioral abnormalities induced by serotonin deficiency", Proceedings of the National Academy of Sciences, 2008, 105(4): 1333-1338.
Blier et al., "Serotonin and beyond: therapeutics for major depression", Philosophical Transactions of the Royal Society B, 2013, 368: 20120536.
Brochet et al., "Effects of Triiodothyronine on the 5-Hydroxytryptophan-Induced Head Twitch and Its Potentiation by Antidepressants in Mice", European Journal of Pharmacology, 1985, 112: 411-414.
Byerley et al., "5-Hydroxytryptophan: A Review of Its Antidepressant Efficacy and Adverse Effects", Journal of Clinical Psychopharmacology, 1987, 7(3): 127-137.
Carlson, L.A., "Niaspan, the prolonged release preparation of nicotinic acid (niacin), the broad-spectrum lipid drug", International Journal of Clinical Practice, 2004, 58(7): 706-713.
Conley et al., "Clinical spectrum of the osmotic-controlled release oral delivery system (OROS), an advanced oral delivery form", Current Medical Research and Opinion, 2006, 22(10): 1879-1892.
Delgado, Pedro, "Monoamine Depletion Studies: Implications for Antidepressant Discontinuation Syndrome", Journal of Clinical Psychiatry, 2006, 67(Suppl. 4): 22-26.
Delgado et al., "Serotonin Function and the Mechanism of Antidepressant Action: Reversal of Antidepressant-Induced Remission by Rapid Depletion of Plasma Tryptophan", Archives of General Psychiatry, 1990, 47: 411-418.
Ebert et al., "Combined SSRI-RIMA treatment in refractory depression: Safety data and efficacy", Psychopharmacology, 1995, 119: 342-344.
Fuxe et al., "Effects of Subchronic Antidepressant Drug Treatment on Central Serotonergic Mechanisms in the Male Rat", Advances in Biochemical Psychopharmacology, 1982, 31: 91-107.
Gallardo et al. "Controlled Release Solid Dosage Forms Using Combinations of (meth)acrylate Copolymers", Pharmaceutical Development and Technology, 2008,13: 413-423.

Gijsman et al., "Placebo-Controlled Comparison of Three Dose-Regimens of 5-Hydroxytryptophan Challenge Test in Healthy Volunteers", Journal of Clinical Psychopharmacology, 2002, 22(2): 183-189.
Haddad, Peter, "Antidepressant Discontinuation Syndromes: Clinical Relevance, Prevention and Management", Drug Safety, 2001, 24(3): 183-197.
Iovieno et al,, "Second-tier natural antidepressants: Review and critique", Journal of Affective Disorders, 2011, 130: 343-357.
Jacobsen et al., "The 5-HT deficiency theory of depression: perspectives from a naturalistic 5-HT deficiency model, the tryptophan hydroxylase $2^{Arg}439^{His}$ knockin mouse", Philosophical Transactions of the Royal Society B, 2012, 367: 2444-2459.
Jacobsen et al., "Deficient serotonin neurotransmission and depression-like serotonin biomarker alterations in tryptophan hydroxylase 2 (Tph2) loss-of-function mice", Molecular Psychiatry, 2012, 17: 694-704.
Levine et al., "Saftee: A Technique for the Systematic Assessment of Side Effects in Clinical Trials", Psychopharmacology Bulletin, 1986, 22(2): 343-346.
Levine et al., "Controlled-Release Oxycodone", The Journal of American Academy of Orthopaedic Surgeons, 2005, 13(1): 1-4.
Martin, Thomas, "Serotonin Syndrome", Annals of Emergency Medicine, 1996, 28(5): 520-526.
Oxycontin, FDA Package Insert, Purdue Pharma, LP, 2009, 32 pages.
Poewe et al., "Treatment of Motor Fluctuations in Parkinson's Disease with an Oral Sustained-Release Preparation of L-Dopa: Clinical and Pharmacokinetic Observations", Clinical Neuropharmacology, 1986, 9(5): 430-439.
Sanchez et al., "Escitalopram, the S-(+)-enantiomer of citalopram, is a selective serotonin reuptake inhibitor with potent effects in animal models predictive of antidepressant and anxiolytic activities", Psychopharmacology, 2003, 167: 353-362.
Steele et al., "A Randomized, Controlled, Effectiveness Trial of OROS-Methylphenidate Compared to Usual Care With Immediate-Release Methylphenidate in Attention Deficit-Hyperactivity Disorder", The Canadian Journal of Clinical Pharmacology, 2006, 13(1): e50-e62.
Thrombre et al., "Osmotic drug delivery using swellable-core technology", Journal of Controlled Release, 2004, 94: 75-89.
TOXNET Toxicology Data Network, "5-Hydroxytryptophan", National Library of Medicine HSDB Database, 17 pages.
Trimble, Michael, "Worldwide Use of Clomipramine", Journal of Clinical Psychiatry, 1990, 51-58.
Verma et al., "Formulation aspects in the development of osmotically controlled oral drug delivery systems", Journal of Controlled Release, 2002, 79: 7-27.
Waterman et al., "Osmotic capsules: A universal oral, controlled-release drug delivery dosage form", Journal of Controlled Release, 2011, 152: 264-269.
Wellington et al., "Venlafaxine Extended-Release: A Review of its Use in the Management of Major Depression", CNS Drugs, 2001, 15(8): 643-669.
Yatham et al., "Positron Emission Tomography Study of the Effects of Tryptophan Depletion on Brain Serotonin$_2$ Receptors in Subjects Recently Remitted From Major Depression", Archives of General Psychiatry, 2012, 69(6): 601-609.
Dreshfield-Ahmad LJ et al. Enhancement in extracellular serotonin levels by 5-hydroxytryptophan loading after administration of way 100635 and fluoxetine. Life Sciences. Apr. 15, 2000; 66(21): 2035-2041, 2000.
Supplementary European Search Report and Opinion, EP 11835206, Mar. 7, 2014.
Examination Report, EP 11835206.1, mailed Dec. 10, 2014.
Arisco AM et al. Oxybutynin extended release for the management of overactive bladder: a clinical review. Drug Design, Development and Therapy. 2009; 3: 151-161.
Bodor ET, Offermanns S. Nicotinic acid: an old drug with a promising future. British Journal of Pharmacology. 2008; 153 Suppl 1: S68-75.

(56) References Cited

OTHER PUBLICATIONS

Croom KF, Wellington K. Modified release nifedipine: a review of the use of modified-release formulations in the treatment of hypertension and angina pectoris. Drugs. 2006; 66(4): 497-528.
Gupta S, Sathyan G. Pharmacokinetics of an oral once-a-day controlled-release oxybutynin formulation compared with immediate-release oxybutynin. Journal of Clinical Pharmacology. 1999; 39: 289-296.
Klausner EA et al. Novel levodopa gastroretentive dosage form: in-vivo evaluation in dogs. Journal of Controlled Release. 2003; 88: 117-126.
Knopp RH et al. Equivalent efficacy of a time-release form of niacin (Niaspan®) given once-a-night versus plain niacin the management of hyperlipidemia. Metabolism. Sep. 1998; 47(9): 1097-1104.
Modi NB et al. Single- and multiple-dose pharmacokinetics of an oral once-a-day osmotic controlled-release OROS® (methylphenidate HCL) formulation. Journal of Clinical Pharmacology. 2000; 40: 379-388.
Sandberg A et al. Design of a new multiple-unit controlled-release formulation of metoprolol—metoprolol CR. European Journal of Clinical Pharmacology. 1988; 33 [Suppl]: S3-S7.
Sandberg A et al. Pharmacokinetic and pharmacodynamic properties of a new controlled-release formulation of metoprolol: a comparison with conventional tablets. European Journal of Pharmacology. 1988; 33 [Suppl]: S9-S14.
AVINZA®, package insert, Pfizer, Inc. Rev. Apr. 20, 2014; 26 pp.
BIAXIN®, package insert, Abbott Laboratories. Rev. Jun. 2002; 25 pp.
ROXICODONE®, package insert, Xanodyne Pharmaceuticals, Inc. Rev. Aug. 2008; 17 pp.
Bang LM and Keating GM. Paroxetine controlled release. CNS Drugs 2004; 18(6): 355-364.
Cunningham LA. Once-daily venlafaxine extended release (XR) and venlafaxine immediate release (IR) in outpatients with major depression. Annals of Clinical Psychiatry. 1997; 9(3): 157-164.
Jacobsen JPR et al. SSRI augmentation by 5-hydroxytryptophan slow release: mouse pharmacodynamic proof of concept. Neuropsychopharmacology. 2016; 1-11.
Lowe SL et al. L-5-hydroxytryptophan augments the neuroendocrine response to a SSRI. Psychoneuroendocrinology. 2006; 31: 473-484.
Jacobsen JPR et al. Differential sensitivity to SSRIs in the tail suspension test in NMRI and C57 mice: relation to brain 5HT levels. European Neuropsychopharmacology The Journal of the European College of Neuropsychopharmacology. Oct. 16, 2007. vol. 17, Suppl 4, S375, 2 pp.

* cited by examiner

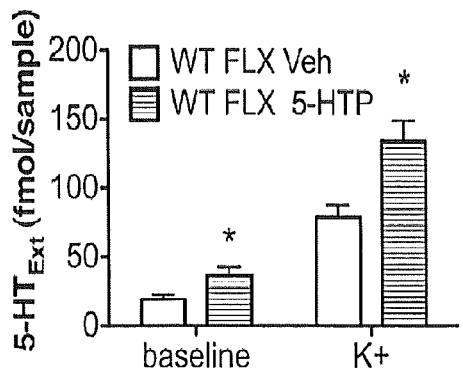 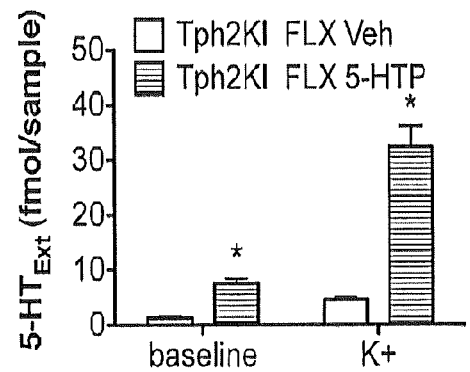
FIG. 10A  FIG. 10B
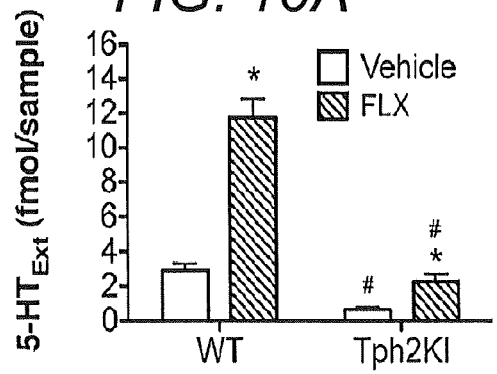 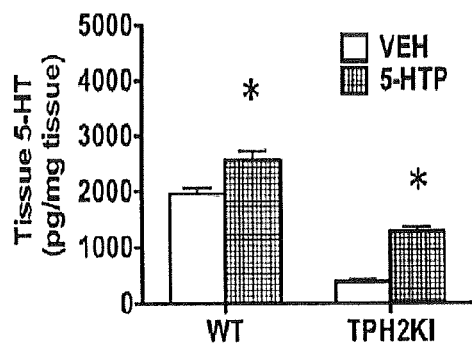
FIG. 10C  FIG. 10D
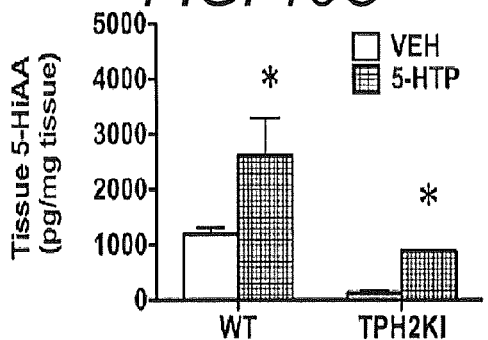 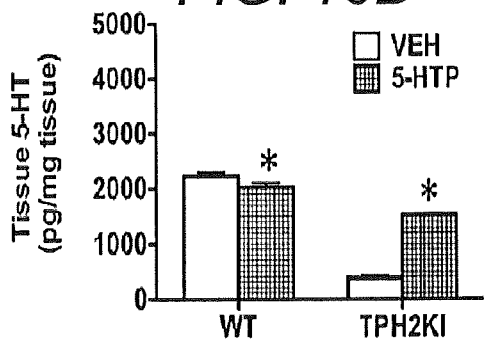
FIG. 10E  FIG. 10F
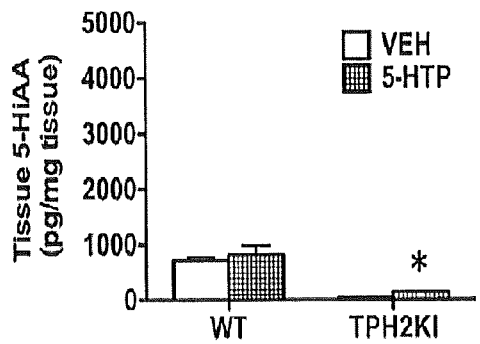
FIG. 10G

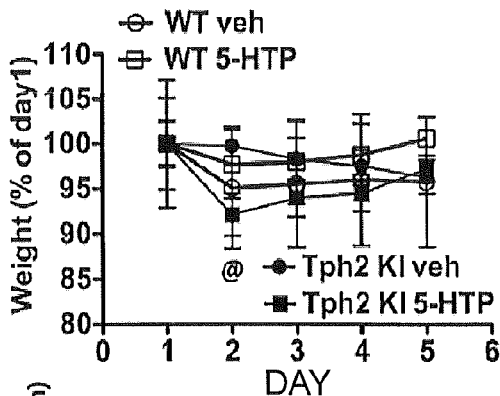
FIG. 11I
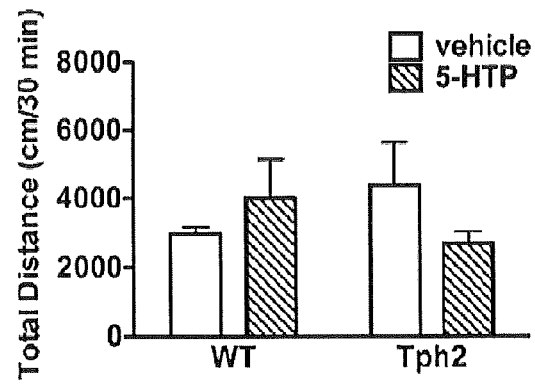
FIG. 11J
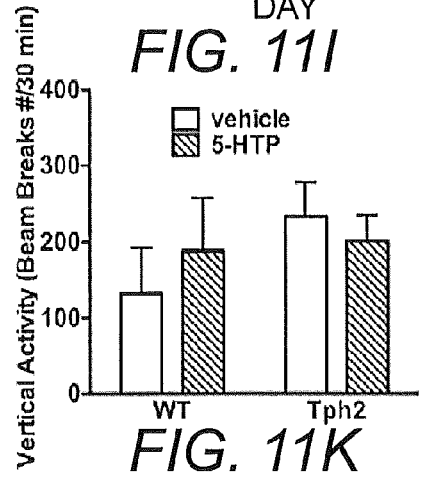
FIG. 11K
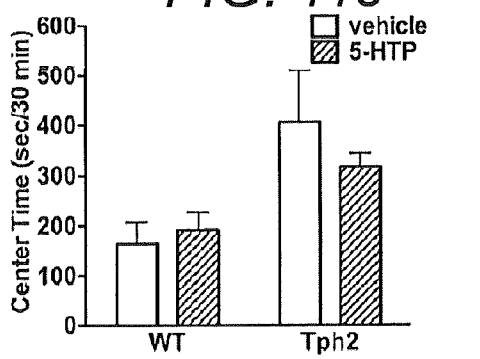
FIG. 11L
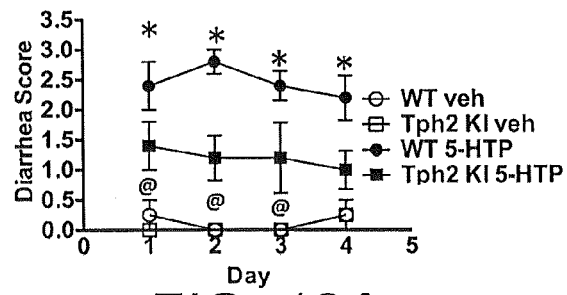
FIG. 12A
FIG. 12B
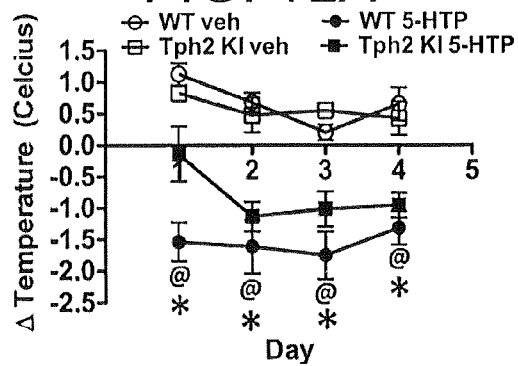
FIG. 12C
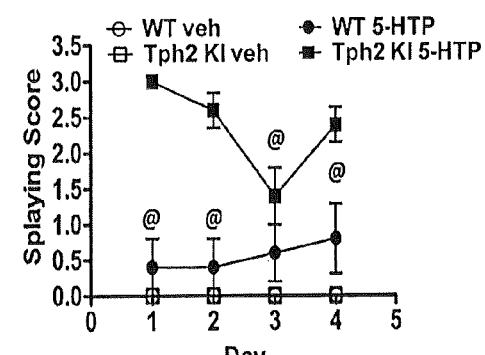
FIG. 12D

SLOW-RELEASE FORMULATIONS OF 5-HYDROXYTRYPTOPHAN AS AN ADJUNCT TO PRO-SEROTONERGIC THERAPIES

RELATED APPLICATIONS

This application is a continuation under 35 U.S.C. 111(a) of PCT Application No. PCT/US2011/057247, filed Oct. 21, 2011, which in turn claims the benefit under 35 U.S.C. §119(e) of U.S. Provisional Patent Application Ser. No. 61/405,831, filed Oct. 22, 2010, and U.S. Provisional Patent Application Ser. No. 61/504,354, filed Jul. 5, 2011, the disclosure of each of which is incorporated herein by reference in its entirety.

STATEMENT OF GOVERNMENT SUPPORT

This invention was made with Government support under grant number MH79201 from the National Institutes of Health. The United States Government has certain rights in this invention.

FIELD OF THE INVENTION

The present invention concerns the treatment of psychiatric disorders, serotonergic dysregulation disorders and/or augmentation of serotonin levels in the brain, and formulations of 5-hydroxytryptophan useful therefor.

BACKGROUND OF THE INVENTION

Dysregulation of serotonergic (or 5-hydroxytryptamine, 5-HT) neurotransmission is believed to be an important contributing factor in numerous psychiatric disorders, including major depression, attention-deficit/hyperactivity disorder (ADHD), schizophrenia, aggression and suicidal behavior. The central serotonergic system is also a primary target for clinical treatment of these disorders. Drugs that target this system include tricyclic antidepressants and serotonin reuptake inhibitors (e.g., SSRIs), as well as psychostimulants and hallucinogenic drugs (see, e.g., Bonasera et al., *Pharmacol. Ther.* 88, 133 (2000); Gingrich et al., *Psychopharmacol.* 155, 1 (2001); Murphy et al., *Genes Brain Behav.* 2, 350 (2003)).

In depression, for example, serotonergic neurotransmission deficiencies have been prominently implicated for more than 40 years. While it remains to be definitively proven that 5-HT deficiency can cause depression, biomarker and post-mortem studies indicate that serotonin deficiency exists in at least some depression patients (Jacobsen et al., Deficient serotonin neurotransmission and depression-like serotonin biomarker alterations in tryptophan hydroxylase 2 (Tph2) loss-of-function mice. *Molecular psychiatry* (May 3, 2011); Meltzer, Serotonergic dysfunction in depression. *Br J Psychiatry Suppl*, 25 (1989); Asberg, Neurotransmitters and suicidal behavior. The evidence from cerebrospinal fluid studies. *Ann N Y Acad Sci* 836, 158 (1997); Correa et al., Prolactin response to D-fenfluramine and suicidal behavior in depressed patients. *Psychiatry Res* 93, 189 (2000)).

On the other hand, it is beyond dispute that drugs that enhance the extracellular level of serotonin treat depression symptoms, at least in moderate to severe cases (Kirsch, I. et al. Initial severity and antidepressant benefits: a meta-analysis of data submitted to the Food and Drug Administration. *PLoS Med* 5, e45, 2008).

However, drugs that enhance serotonin extracellular levels in the brain, such as selective serotonin reuptake inhibitors (SSRIs), alleviate depression symptoms only in about 50% of patients, leaving a large treatment-resistant depression (TRD) population (Fava, Diagnosis and definition of treatment-resistant depression. *Biological psychiatry* 53, 649 (2003)). Add-on of a second serotonin enhancing agent to SSRI treatment may augment clinical efficacy (Blier et al., Mirtazapine and paroxetine in major depression: a comparison of monotherapy versus their combination from treatment initiation. *Eur Neuropsychopharmacol* 19, 457 (2009); Blier et al., Potential mechanisms of action of atypical antipsychotic medications in treatment-resistant depression and anxiety. *J Clin Psychiatry* 66 Suppl 8, 30 (2005)), indicating that insufficient increase of extracellular serotonin levels may be causal in at least some SSRI TRD.

SUMMARY OF THE INVENTION

Provided herein is 5-HTP included in or provided as slow-release formulations (e.g., delayed release formulation, sustained release formulation, drug depot formulation, etc.), which are useful to improve the drugability of 5-HTP as well as improve the efficacy of pro-serotonergic medications in the treatment of psychiatric and other disorders related to serotonin dysregulation.

Also provided are methods of treating a subject for a serotonergic neurotransmission dysregulation disorder including administering to said subject 5-hydroxytryptophan (5-HTP) at a slow rate. In some embodiments, the 5-HTP is administered in combination with a serotonin enhancer, said 5-HTP administered in an amount effective to enhance the effects of the serotonin enhancer. In some embodiments, the subject in being treated with a serotonin enhancer (e.g., subject has been treated with the serotonin enhancer for at least 2, 3 or 4 weeks).

In some embodiments, the 5-HTP is provided in an amount effective to increase extracellular levels of serotonin in the brain as compared to the levels upon serotonin enhancer treatment without the 5-HTP administration.

In some embodiments, the 5-HTP is provided in or as an oral formulation. In some embodiments, the 5-HTP is provided in or as a transdermal formulation.

Also provided is a formulation such as a patch for transdermal administration comprising: a) a backing; and b) a drug layer comprising 5-hydroxytryptophan (5-HTP), or a pharmaceutically acceptable salt or prodrug thereof; said patch configured to administer said 5-HTP transdermally. In some embodiments, the patch is a single-layer drug-in-adhesive patch, a multi-layer drug-in-adhesive patch, a reservoir-type patch, a matrix-type patch or a monolithic patch.

Further provided is 5-HTP included in or provided as slow-release formulation for use in the treatment of a serotonergic neurotransmission dysregulation disorder. In some embodiments, the 5-HTP is included in or provided as a slow-release formulation for use as an adjunct (add-on) to a serotonin enhancer therapy. Also provided is the use of a 5-HTP formulation as provided herein in the manufacture of a medicament for the treatment of a serotonergic dysregulation disorder (e.g., as an adjunct to a serotonin enhancer therapy).

The foregoing and other objects and aspects of the present invention are explained in greater detail in the drawings herein and the specification set forth below.

BRIEF DESCRIPTION OF THE DRAWINGS

FIGS. 10A-10G. Subcutaneous (sc) administration of 5-HTP enhanced the 5-HT$_{Ext}$ response to chronic fluoxetine (FLX) and increased 5-HT tissue levels in mice not treated with FLX. 10A: 5-HTP SR (100 mg/kg/d) two-fold enhanced the 5-HT$_{Ext}$ response to chronic FLX in WT mice at baseline and following neuronal depolarization with K$^+$. 10B: 5-HTP SR seven-fold enhanced the 5-HT$_{Ext}$ response to chronic FLX in Tph2KI mice, a mouse model of 5-HT deficiency, at baseline and following neuronal depolarization with K$^+$. Note x-axis scale differences between 10A and 10B. 10C: For reference, while chronic FLX fold-wise enhanced 5-HT$_{Ext}$ similarly in WT and Tph2KI mice, the levels of FLX treated Tph2KI mice barely reached the levels of untreated WT. 10D-10E: 5-HTP SR increased tissue 5-HT (10D) and 5-HIAA (10E) in both genotypes. 10E-10G: 5-HTP IR (50 mg/kg, sc 8 h post-injection, after 4 d of 2×50 mg/kg) increased tissue 5-HT in Tph2KI mice (10F), but caused a small 5-HT decrease at this time point in WT mice. A small increase in 5-HIAA levels were also observed in Tph2KI mice (10G). *, p<0.05, vehicle vs 5-HTP or vehicle vs FLX C). #, p<0.05, WT vs Tph2KI, C). T-test. N-7-10, microdialysis. N=4-6, tissue 5-HT and 5-HIAA.

FIGS. 11A-11L. Virtually no 5-HT associated side-effects in response to SC 5-HTP SR treatment in mice maintained on chronic FLX. 11A-11D: Day of treatment start. No occurrence of diarrhea (11A), tremor (11B) or temperature changes (11C) but perhaps a slight, non-significant increase in splaying in the Tph2KI mice (11D) in response to 5-HTP SR. 11E-11I: Day 2-4 of treatment: No occurrence of diarrhea (11E), tremor (11F), temperature changes (11G) or abnormal splaying (11H), but a transient decrease in body weight (11I) in the Tph2KI mice only at day 1. 11J-11L: Day 5: No effect on locomotor and anxiety-like behavior in the open field. *, p<0.05, WT, vehvs 5-HTP. @, p<0.05, Tph2PKI, vehvs 5-HTP. T-test or 2way RM-ANOVA. N=4-6

FIGS. 12A-12I. Marked 5-HT associated side-effects in response to 5-HTP immediate release (IR) (2×50 mg/kg/day, S.C.) in mice maintained on chronic FLX. 12A-12F: 5-HT side-effects followed over first 4 days of treatment following AM 5-HTP IR administration. 5-HTP IR caused marked occurrence of diarrhea (12A), tremor (12B), hypothermia (12C), splaying (12D) and head-twitches (12F). Body Weights were only minorly and transiently affected in Tph2KI mice (12E). 12G-12I: Day 5: 5-HTP IR suppressed locomotion and increased anxiety-like behaviors in the open field in Tph2KI mice, while in WT mice only vertical activity was significantly suppressed, although a trend for suppression was observed for total distance. *, p<0.05, WT, vehvs 5-HTP. @, p<0.05, Tph2PKI, vehvs 5-HTP. T-test or 2way RM-ANOVA. N=4-6.

DETAILED DESCRIPTION OF THE PREFERRED EMBODIMENTS

Figure 1:
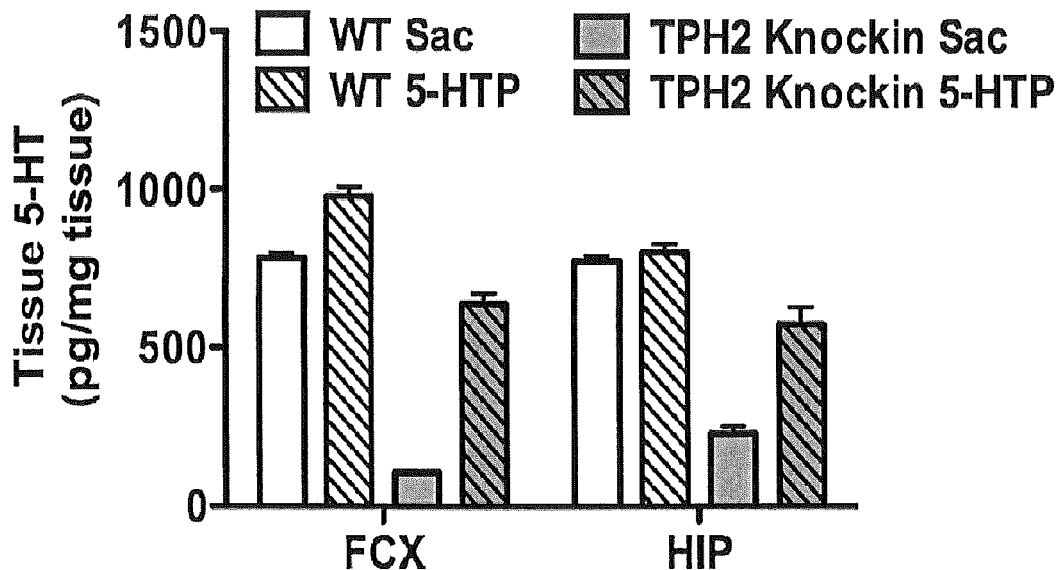
FIG. 1. 5-HTP in drinking water (4 mg/ml≈320 mg/kg/day, no carbidopa) restores brain 5-HT in 5-HT deficient mice FIGS. 2A-2B. Body weight decrease observed after 5-HTP 4 mg/ml (FIG. 2A). No diarrhea and no obvious malaise were observed, so the decrease is likely due to decreased drinking (FIG. 2B).

The present invention is explained in greater detail below. The disclosures of all references cited herein are incorporated by reference to the extent they are consistent with the description presented herein.

A. 5-HTP Slow-Release Formulations

"5-hydroxytryptophan" or "5-HTP" is the precursor of serotonin (5-HT) in the body. Though known as a dietary supplement and experimentally used in the treatment of depression, appropriate, well-controlled studies of 5-HTP antidepressant efficacy are lacking. Indeed, preclinical studies indicate that 5-HTP administration alone has surprisingly small effects on extracellular serotonin. However, 5-HTP appears to augment the extracellular serotonin response to acute SSRI treatment (Perry, K. W. & Fuller, R. W. Extracellular 5-hydroxytryptamine concentration in rat hypothalamus after administration of fluoxetine plus L-5-hydroxytryptophan. *J Pharm Pharmacol* 45, 759-761 (1993); Jacobsen, J. P. et al. Insensitivity of NMRI mice to selective serotonin reuptake inhibitors in the tail suspension test can be reversed by co-treatment with 5-hydroxytryptophan. Psychopharmacology 199, 137-150, (2008)) [cite?] In addition, administration of 5-HTP can lead to side effects (e.g., gastrointenstinal effects such as nausea, vomiting and diarrhea), dizziness, euphoria and mood changes, typically upon administration (Turner, E. H., Loftis, J. M. & Blackwell, A. D. Serotonin a la carte: supplementation with the serotonin precursor 5-hydroxytryptophan. *Pharmacol Ther* 109, 325-338, (2006)).

This may to due to 5-HTP's rapid absorption-elimination profile (Gijsman H. J. et al. Placebo-controlled comparison of three dose-regimens of 5-hydroxytryptophan challenge test in healthy volunteers. *J Clin Psychopharmacol*. April; 22(2):183-9 (2002)), which conceivably can result in overdose upon administration followed by withdrawal upon quick elimination in the body. This aspect, the above mentioned moderate effect of 5-HTP alone on extracellular 5-HT combined with the availability of alternatives to enhance extracellular serotonin levels, can explain its limited use in the clinical setting.

As used herein, "slow-release 5-HTP" refers to a formulation with the ability to release 5-HTP at a slow rate, such that the plasma $T_{1/2}$ is delayed and/or $T_{max}$ is decreased as compared to an immediate release formulation. The terms "5-HTP at a slow rate" and "5-HTP at a slow release" are used interchangeably and refer to the ability to cause the 5-HTP to be released in the subject at a slower rate than if administered directly.

In some embodiments, the slow-release formulation comprises 5-HTP in or as a delayed release formulation, sustained release formulation and/or drug depot formulation. See, e.g., U.S. Pat. No. 8,029,822 to Faour et al.; U.S. Pat. No. 8,021,687 to Hirsh et al.; U.S. Pat. No. 8,017,152 to Gustafsson et al.; U.S. Pat. No. 8,007,826 to Blight et al.; U.S. Pat. No. 7,914,804 to O'Neil et al.; U.S. Pat. No. 7,906,141 to Ziegler et al.; U.S. Pat. No. 7,897,173 to Ziegler et al.; U.S. Pat. No. 7,964,215 to Ganesan et al.; U.S. Pat. No. 7,709,024 to Kadum et al.; U.S. Pat. No. 7,741,273 to McKay; U.S. Pat. No. 7,645,460 to Dansereau et al.; and U.S. Pat. No. 5,658,587 to Santus et al., which are incorporated by reference herein.

"Sustained release" formulations release drug at a predetermined rate and/or release in a manner that maintains the drug as a substantially constant level (e.g., plasma level) for a set period of time. Examples of sustained release formulations include, but are not limited to, oral formulations (e.g., enteral, buccal/sublabial/sublingual, respiratory), ocular/otologic/nasal formulations, dermal formulations (e.g., ointment, paste, film, hydrogel, liposomes, dermal patch, transdermal patch, transdermal spray), injection/infusion (e.g., intradermal, subcutaneous, transdermal implant, intramuscular).

In some embodiments, the slow-release formulation employs a gastro-retentive principle, delivering the 5-HTP in a slow release in the ventricle and/or upper intestine using for instance buoyant systems, high density systems, magnetic systems, mucoadhesive systems, swelling/expanding systems, superporous hydrogels and systems utilizing the inclusion of gastric motility retarding agents with biocompatible polymeric materials (Murphy C. S. et al. Gastroretentive drug delivery systems: current developments in novel system design and evaluation. *Curr Drug Deliv*. October; 6(5):451-60 (2009)).

In some embodiments, the slow-release formulation employs oral hydrophilic or lipophilic matrix tablets. In some embodiments, the slow-release formulation employs oral osmotic systems, for instance the asymmetric membrane technology or swellable core technology. In some embodiments, the slow-release formulation employs oral multiparticulate systems (Thombre A G. Assessment of the feasibility of oral controlled release in an exploratory development setting. *Drug Discov Today*. September 1; 10(17): 1159-66 (2005)).

For example, immediate-release oral 5-HTP typically has a $T_{1/2}$ of 2-3 hours, and thus a 5-HTP at a slow rate would have a $T_{1/2}$ greater than 3, 4, 5, 6 or 7 hours. In some embodiments, the $T_{1/2}$ is at least 8 hours. In some embodiments, the $T_{1/2}$ is from 8, 10 or 12 hours to 24, 48 or 72 hours.

As another example, immediate-release oral 5-HTP has a $T_{max}$ of 1-2 hours. Thus, in some embodiments, the slow-release 5-HTP is administered and/or formulated such that the $T_{max}$ (time of maximal plasma concentration after administration) of 5-HTP is at least 2 hours, or between 2 hours and 12 hours.

In some embodiments, 5-HTP is provided in a therapeutically effective amount in a formulation suitable for oral administration. As used herein, the term "therapeutically effective amount" refers to that amount of compound that is sufficient to show a benefit in the subject. In some embodiments, the formulation is provided in a unit dose for once-daily or twice-daily use. See U.S. Patent application publication no. 2010/0298379 to Jacobsen et al., which is incorporated by reference herein in its entirety.

In some embodiments, a daily dose of 0.05 to 10 grams may be provided (e.g., as one tablet for daily dosing, or two tablets for twice-daily dosing with half the daily dosage in each). In some embodiments, the daily dose may be from 0.01, 0.05, 0.1, 0.2, 0.5, or 0.75, to 5, 8, or 10 grams per day. In some embodiments, the daily dose may be from 1 to 5 grams per day. In some embodiments, the daily dose may be from 1 to 3 grams per day.

In some embodiments, 5-HTP is administered so as to achieve plasma 5-HTP levels averaging 10-100 ng/ml. In some embodiments, 5-HTP is administered so as to achieve plasma 5-HTP levels averaging 100-1000 ng/ml.

In a particular embodiment, 5-HTP is provided in a formulation suitable for transdermal administration. In some embodiments, the formulation is suitable for 1, 2, 3, 5, 7, 10, 12, 14, or 30-day transdermal administration. In some embodiments, transdermal administration may have the advantage that gastrointestinal (GI) 5-HT formation is reduced, thereby lessening GI side effects (common from 5-HTP and other pro-serotonergic compounds). Transdermal administration may, therefore, allow for higher plasma 5-HTP levels without the occurrence of significant GI side effects and achieve better efficacy.

In some embodiments, 5-HTP, a pharmaceutically acceptable salt, or prodrug thereof, is formulated for transdermal administration. In some embodiments, the formulation is in the form of a "patch." The patch may be a single-layer drug-in-adhesive patch, a multi-layer drug-in-adhesive patch (typically also including a membrane such as a rate-controlling membrane between at least two of the layers), a reservoir-type patch, a matrix-type or monolithic patch, etc.

In some embodiments, the patch includes a backing, an adhesive drug layer, and a release liner. In some embodiments, the patch further includes a second adhesive layer (with or without drug), and in some embodiments a membrane (e.g., a rate-controlling membrane) is positioned between a first and second adhesive layer. See also US Patent Application Publication nos. 2003/0109512 to Kucharchuk et al. and 2005/0163831 to Ikesue et al., which are each incorporated by reference herein.

For embodiments including a backing, any backing may be used without particular limitation, and a stretchable or an unstretchable backing may be used. Specific examples of the backing include cloth, nonwoven cloth, polyurethane, polyester, polyvinyl acetate, polyvinylidene chloride, polyethylene, polyethylene terephthalate and aluminum sheet, one made of complex material thereof, and the like.

In some embodiments, an adhesive layer comprising an adhesive base agent and 5-HTP may be placed on the backing. The amount of 5-HTP in some embodiments is 0.1-50 weight % of the total weight in the adhesive layer. In some embodiments the adhesive layer may include an adhesive agent such as a rubber polymer, an acrylic polymer, or a combination thereof. In some embodiments the base adhesive agent is 10-90 weight % of the total weight of the adhesive layer.

Examples of rubber polymers include, but are not limited to, styrene-isoprene-styrene copolymer, polyisobutylene, isoprene rubber, styrene-butadiene-styrene copolymer, styrene-butadiene rubber and silicone rubber. These polymers may be used individually or in combination. Examples of acrylic polymers include, but are not limited to, polymers employing alkyl(meth)acrylate esters in which carbon number in the alkyl group is 4 or more and/or 15 or less. Specific examples of such alkyl(meth)acrylate ester include alkyl (meth)acrylate esters having a linear alkyl group, a branched alkyl group such as butyl, pentyl, hexyl, heptyl, octyl, nonyl, decyl, undecyl, dodecyl and tridecyl. These polymers may be used individually or in combination.

Further, a copolymerizable monomer may be copolymerized in the alkyl(meth)acrylate ester, if desired. Examples of the monomer include carboxyl group containing monomers such as (meth)acrylic acid, itaconic acid, maleic acid or maleic anhydride; sulfoxyl group containing monomers such as styrenesulfonate, allylsulfonate, sulfopropyl(meth) acrylate, (meth)acryloyloxynaphthalenesulfonic acid or acrylamide methylpropanesulfonic acid; hydroxyl group containing monomers such as hydroxyethyl(meth)acrylate ester or hydroxypropyl(meth)acrylate ester; amide group containing monomers such as (meth)acrylamide, dimethyl (meth)acrylamide, N-butylacrylamide, N-methylol(meth) acrylamide or N-methylolpropane(meth)acrylamide; alkylaminoalkyl group containing monomers such as aminoethyl (meth)acrylate ester, dimethylaminoethyl(meth)acrylate ester or tert-butylaminoethyl(meth)acrylate ester; alkoxyalkyl(meth)acrylate esters such as methoxyethyl(meth)acrylate ester or ethoxyethyl(meth)acrylate ester; an alkoxy group (or ether bond in a side chain) containing (meth) acrylic esters such as tetrahydrofurfuryl(meth)acrylate ester, methoxyethylene glycol(meth)acrylate ester, methoxydiethylene glycol(meth)acrylate ester, methoxypolyethylene glycol(meth)acrylate ester or methoxypolypropylene glycol (meth)acrylate ester; and vinyl-series monomers such as (meth)acrylonitrile, vinyl acetate, vinyl propionate, N-vinyl-2-pyrrolidone, methylvinyl pyrrolidone, vinyl pyridine, vinyl piperidone, vinyl pyrimidine, vinyl piperazine, vinyl pyrazine, vinyl pyrrole, vinyl imidazole, vinyl caprolactam, vinyl oxazole and vinyl morpholine. One kind of or two kinds or more in combination of these may be copolymerized. These copolymerizable monomers can be used for the purpose of adjusting cohesion force of the adhesive layer or enhancing solubility of the drug. The copolymerization amount may be within a range of 2-40% by weight according to some embodiments.

In some embodiments, the adhesive layer may include as a permeation enhancer compounds that are conventionally recognized to have a permeation enhancing effect on the skin. Examples include, but are not limited to, fatty acids having 6 to 20 carbon atoms, aliphatic alcohols, fatty acid esters, fatty acid amides, and fatty acid ethers, aromatic organic acids, aromatic alcohols, aromatic organic acid esters and ethers, which may be saturated or unsaturated, and also may be linear, branched or cyclic, lactic acid esters, acetic acid esters, monoterpenes, sesquiterpenes, Azone, Azone derivatives, glycerin fatty acid esters, propylene glycol fatty acid esters, sorbitan fatty acid esters (Span), polysorbates (Tween), polyethylene glycol fatty acid esters, polyoxyethylene hydrogenated castor oils (HCO), polyoxyethylene alkyl ethers, sucrose fatty acid esters and vegetable oils. Examples include caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanol amide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, L-menthol, borneol, d-limonene, isoeugenol, isoborneol, nerol, dl-camphor, glycerin monocaprirate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane and olive oil. Such permeation enhancers may be used alone or in combination. In some embodiments, the permeation enhancer is present in a range of 0.1 to 10 or 20 weight % of the total weight of the adhesive layer.

In some embodiments, the adhesive layer may include a plasticizer. Examples include, but are not limited to, petroleum oil (paraffin process oil, naphthene process oil, aromatic process oil and the like), squalane, squalene, vegetable oil (olive oil, camellia oil, castor oil, tall oil, peanut oil and the like), silicone oil, dibasic acid ester (dibutyl phthalate, dioctyl phthalate and the like), liquid rubber (polybutene, liquid isoprene rubber and the like), liquid fatty acid ester (isopropyl myristate, hexyl laurate, diethyl sebacate, diisopropyl sebacate and the like), polyhydric alcohol (diethylene glycol, polyethylene glycol, glycol salicylate, propylene glycol, dipropylene glycol and the like), triacetin, triethyl citrate, crotamiton and the like. Among these plasticizers, polyhydric alcohols, liquid paraffin, liquid polybutene, crotamiton, diethyl sebacate and hexyl laurate are more preferable, and polyethylene glycol is especially preferable. These plasticizers may be used alone or in combination.

In some embodiments, the formulation contains only 5-HTP as primary or the only active ingredient in the patch.

In some embodiments, administration of 5-HTP is subject to the proviso that the subject is not also concurrently administered a peripheral decarboxylase inhibitor. In some embodiments, such concurrent administration have been found to unexpectedly increase rather than decrease side effects, while having no obvious clinical benefit, despite decreasing 5-HTP peripheral degradation and enhancing 5-HTP plasma levels. Peripheral decarboxylase inhibitors include carbidopa, benserazide, methyldopa, etc. See, e.g., U.S. Pat. No. 6,387,936.

In some embodiments, administration of 5-HTP is subject to the proviso that a steroidal drug such as testosterone, estrogen, progesterone, etc., is not administered in combination therewith.

B. Use of 5-HTP Slow-Release Formulation as an Adjunct to Pro-Serotonergic Therapies The 5-HTP formulations taught herein according to some embodiments are useful in the treatment of a psychiatric disorder/serotonergic neurotransmission dysregulation disorder. In some embodiments, the 5-HTP is used as an adjunct therapy and is administered in combination with a serotonin enhancer such as an SSRI, MAOI, TCA, etc.

"Serotonergic neurotransmission dysregulation disorder" as used herein refers to any disorder in which a decrease in available serotonin is believed to contribute, at least in part, to a disease, disorder, or condition and/or is treatable by enhancing serotonergic neurotransmission. Examples of such disorders include, but are not limited to, depressive disorder (e.g., major depression), anxiety disorder, social anxiety disorder, generalized anxiety disorder, bipolar disorder, schizophrenia, autism, epilepsy, mood disorders, alcohol or substance abuse and associated disorders, panic disorder, migraine, tension headache, obesity, bulimia, anorexia, premenstrual syndrome, menopause, sleep disorders (e.g., sleep apnea, narcolepsy, insomnia), attention-deficit/hyperactivity disorder (ADHD), Tourette syndrome, aggression, obsessive compulsive disorder, pathological gambling, novelty seeking, borderline personality disorders, antisocial personality disorder, suicidality, eating disorders, sexual dysfunction, dementia, social phobia, fibromyalgia, overactive bladder, chronic fatigue syndrome, chronic pain, sudden infant death syndrome, post-traumatic stress syndrome, and Alzheimer's disease. These terms have their usual meaning in the art (see, e.g., DSM-IV), and reference thereto includes the display of one or more symptoms of the disorder as well as a formal diagnosis of the same.

In some embodiments, the serotonergic neurotransmission dysregulation disorder is depression, anxiety, suicidality, obsessive compulsive disorder (OCD), or attention deficit hyperactivity disorder (ADHD).

"Depressive disorder" or "depression" is a mood disorder in which feelings of sadness, loss, anger, or frustration interfere with everyday life for a significant period of time. Depression may be caused by chemical imbalances in the brain, which may in some instances be hereditary. Depression may also be precipitated by events in a person's life. Symptoms of depression may include one or more of: agitation, restlessness, and irritability; a significant change in appetite, often with weight gain or loss; difficulty concentrating; fatigue and lack of energy; feelings of hopelessness and helplessness, or feelings or anger or discouragement; feelings of worthlessness, self-hate, and inappropriate guilt; inactivity and withdrawal from usual activities, a loss of interest or pleasure in activities that were once enjoyed; thoughts of death or suicide; trouble sleeping or excessive sleeping.

"Major depressive disorder" or "major depression" (also called "unipolar depression" or "unipolar major depression") as used herein has its usual meaning in the art, and is typically characterized by the presence of at least five of the depression symptoms noted above for at least two weeks.

"Treatment-resistant depression" or "TRD" is depression that is not treated to remission by an antidepressant (e.g., an SSRI/SNRIs), i.e., typically operationally defined as not treated to remission after two adequate trials of antidepressants (Fava, M. Diagnosis and definition of treatment-resistant depression. *Biological Psychiatry* 53, 649-659, (2003)). This may include an absence or minimal improvement in symptoms upon treatment (e.g., with continuing treatment for more than 4, 5, 6, 7, or 8 weeks), an improvement but later recurrence of symptoms despite continuing treatment, etc.

"Anxiety disorder" or "anxiety" is abnormal or pathological fear or phobia, and may be continuous or episodic. Symptoms of anxiety may include one or more of: mental apprehension, physical tension, and physical symptoms such as panic attacks or symptoms associated with hyperventilation.

"Suicidality" is the intention of taking one's life. Factors which may be considered in making a diagnosis include one or more of: the patient's history, including a history of previous attempts or a family history of suicide; answers during clinical interview in which the subject is asked whether they are presently thinking of suicide, whether they have made actual plans to do so, whether they have thought about the means, and/or what they think their suicide will accomplish; a suicide note, if any; information from friends or relatives; outcomes of psychiatric tests such as the Beck Depression Inventory (BDI), the Depression Screening Questionnaire, and the Hamilton Depression Rating Scale; and the patient's mood, appearance, vocal tone, and similar factors.

"Obsessive compulsive disorder" is a type of anxiety disorder primarily characterized by repetitive obsessions (distressing, persistent, and intrusive thoughts or images) and/or compulsions (urges to perform specific acts or rituals). Often the process is entirely illogical and/or inexplicable. For example, a compulsion of walking in a certain pattern may be used to alleviate an obsession of impending harm.

"Attention deficit hyperactivity disorder" is an abnormal problem (considering the normal range based on a subject's age and development) with inattentiveness, over-activity, and/or impulsivity. Though the cause of ADHD is unknown, imaging studies of the brains of children with ADHD suggest that there may be an imbalance of neurotransmitters (e.g., dopamine, serotonin, and adrenaline) associated with the disorder.

"Substance abuse" as used herein has its usual meaning and includes both alcohol abuse or addiction (e.g., alcoholism, or alcoholic subjects), as well as abuse or addiction to drugs such as narcotics, opiates, stimulants, depressants, etc. (e.g., barbiturates, ecstasy, cocaine, crack cocaine, morphine, heroin, amphetamine, methamphetamine, oxycontin, etc.).

There is some evidence in the literature of the effectiveness of 5-HTP as an add-on treatment in depression. For example, Nardini et al. assigned 26 inpatients to clomipramine 50 mg+placebo or clomipramine+5-HTP 300 mg for four weeks; double-blind scoring using HAMD. A lenient statistical approach was applied to get significances, but it seems fairly clear that 5-HTP enhanced clomipramines effect. Dosing schedule and side effects was not reported upon (Nardini M et al. Treatment of depression with L-5-hydroxytryptophan combined with chlorimipramine, a double-blind study. *Int J Clin Pharmacol Res.;* 3(4):239-50. (1983)). Alino et al. assigned 30 inpatients to nialamid (a MAOI) 300 mg+placebo or nialamid+5-HTP 300 mg for two weeks; double-blind scoring using HAMD. 5-HTP+nialamid were significantly better than nialamide alone at endpoint. Twice daily dosing was used. Side effects were "typical of ADs" and severity did not differ between the groups (Aliño J. J. et al. 5-Hydroxytryptophan (5-HTP) and a MAOI (nialamide) in the treatment of depressions. A double-blind controlled study. *Int Pharmacopsychiatry.* 11(1):8-15 (1976)). van Heile treated 99 chronic treatment resistant out-patients, mostly on TCAs, with add-on 5-HTP ~200 mg+the PDI carbidopa in a open label add-on study. Forty-three patients went into remission. Once (5-HTP) and thrice (carbidopa) daily dosing was used. Side effects were nausea, vomiting and diarrhea, but the severity was greatly decreased when enteric coated 5-HTP capsules were used (van Hiele L J. 1-5-Hydroxytryptophan in depression: the first substitution therapy in psychiatry? The treatment of 99 out-patients with 'therapy-resistant' depressions. *Neuropsychobiology.* 6(4):230-40(1980)). van Praag treated 7 chronic treatment resistant out-patients with clomipramine 50 mg+with 5-HTP ~2-400 mg+the PDI MK 486. Four patients improved, two dropped out due to GI symptoms, one had no change. Dosing schedule was not reported (van Praag H. M. et al. 5-hydroxytryptophan in combination with clomipramine in "therapy-resistant" depressions. *Psychopharmacologia.* 38(3):267-9 (1974)).

In some embodiments, being already treated with a serotonin enhancer minimizes side effects experienced by a subject with initiation of 5-HTP adjunct administration. Therefore, in some embodiments the subject has been taking a serotonin enhancer for at least 5 days, 1, 2, 3, 4 or 5 weeks, or 1, 2, 4, 6, or 12 months before the initiation of 5-HTP coadministration.

Subjects that may be treated in accordance with the present disclosure are, in general, mammalian subjects (e.g., rodent subjects such as mouse or rat, primate subjects such as human or monkey, dog, cat, rabbit, etc.), including male and female subjects. The subject may be of any race and any age, including juvenile, adolescent, and adult.

"Treating" as used herein means the medical management of a subject, e.g., a human patient, with the intent to cure, ameliorate, stabilize, prevent, and/or delay the onset of a disease, pathological condition, or disorder, or one or more symptoms thereof. "Treating" may include submitting or subjecting a subject to a compound which will promote the reduction of symptoms of a disease, or which will slow the progression of said disease, alone or in combination with other indicated therapies, e.g., psychiatric therapy, dietary therapy, etc. For example, a subject may be treated with the administration of synthesized organic molecules, naturally occurring organic molecules, peptides, polypeptides, nucleic acid molecules, and components thereof, and/or psychiatric therapy, electroconvulsive therapy, modulation of dietary intake of amino acids such as tryptophan (which is metabolized into serotonin) and/or tyrosine (which is metabolized into dopamine), etc. "Treating" is also intended to include the act of not giving a subject a contra-indicated therapeutic.

Subjects may be those previously determined to be non-responsive or insufficiently responsive to treatment therapy with a serotonin enhancer such as a serotonin reuptake inhibitor alone, for example, subjects who exhibited no benefit or improvement in symptoms with administration of a serotonin enhancer such as a serotonin reuptake inhibitor; subjects who exhibited insufficient benefit or improvement in symptoms with administration of a serotonin enhancer such as a serotonin reuptake inhibitor; or subjects who exhibited a decrease over time in benefit or improvement in symptoms with administration of a serotonin enhancer such as a serotonin reuptake inhibitor.

In some embodiments, subjects may be screened (e.g., genotyped) for a Tph2 mutation and/or low serotonin levels, for instance by using serotonin biomarkers (Jacobsen J. P. et al. Deficient serotonin neurotransmission and depression-like serotonin biomarker alterations in tryptophan hydroxylase 2 (Tph2) loss-of-function mice. *Mol Psychiatry.* 2011 May 3. [Epub ahead of print]), prior to initiation of the treatments described herein. Such subjects may be more confidently administered the treatments described herein based on a greater expectation of likely clinical benefit of these treatments, based on the greater understanding of the underlying genetic and physiological basis of the disorder as described herein.

"Tryptophan hydroxylase 2" or "Tph2" is the brain-expressed form of tryptophan hydroxylase, which is the rate-limiting enzyme in the synthesis of serotonin ("5-hydroxytryptamine" or "5-HT"). Tph2 consists of an N-terminal regulatory domain, a catalytic domain and a C-terminal tetramerization domain, and belongs to the superfamily of aromatic amino-acid hydroxylases including tyrosine hydroxylase, phenylalanine hydroxylase and Tph1. Tryptophan hydroxylase functions in the body to convert tryptophan to 5-hydroxytryptophan ("5-HTP"), which is then decarboxylated by aromatic amino acid decarboxylase ("AADC") to serotonin, as illustrated in the scheme presented below:

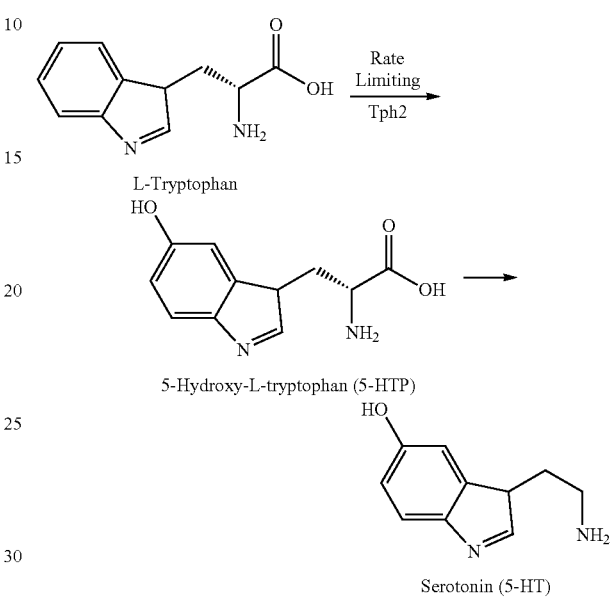

"Serotonin enhancer" as used herein refers to any compound that increases, directly or indirectly, the availability of serotonin in the central nervous system for binding to serotonin receptors at the post-synaptic membrane, and includes, but is not limited to, serotonin reuptake inhibitors, monoamine oxidase inhibitors, tricyclic antidepressants, serotonin agonists, amphetamines, serotonin precursors, serotonin prodrugs, intermediates in the biosynthesis of serotonin, co-factors, and pharmaceutically acceptable salts thereof. Such compounds may be given alone or in combination with other serotonin enhancers.

If not receiving a serotonin enhancer therapy, a subject screened or genotyped according to the present invention and found to have a Tph2 variant may be administered a serotonin enhancer and/or other appropriate treatment as a therapy for a serotonin neurotransmission dysregulation disorder in accordance therewith. If receiving a serotonin enhancer therapy, a subject screened or genotyped according to the present invention may have a previously prescribed serotonin enhancer therapy adjusted and/or discontinued in favor of an alternate treatment, or adjusted to include other suitable treatments (such as 5-HTP coadministration) in addition to the serotonin enhancer therapy.

In other embodiments, however, a subject may be administered a slow release 5-HTP formulation as taught here without such screening for a Tph2 variant and/or low serotonin levels, particularly since the 5-HTP formulations in some embodiments show good tolerability with little to no side effects. For example, a subject currently taking a serotonin enhancer may be administered a 5-HTP formulation as taught herein to determine whether a benefit is seen, for example if the 5-HTP can render a treatment-resistant subject responsive to the serotonin enhancer with a small risk of side effects.

As taught herein, the 5-HTP formulation may also increase endogenous extracellular serotonin levels in the brain in subjects having normal serotonin levels. Normoserotonergic individuals with depression may still be treatment-resistant to serotonin enhancers despite a significant enhancement of extracellular serotonin, for instance, but not restricted to, if signaling via one or more serotonin receptors is dysfunctional. Therefore, in some embodiments, the subject may be treatment-resistant despite significant enhancement of extracellular serotonin levels and may be administered a 5-HTP formulation herein to enhance the effect of the serotonin enhancer, which may further increase the extracellular serotonin levels. In other embodiments, the patient is not treatment-resistant to serotonin enhancers, but is nonetheless co-administered 5-HTP slow release to further augment the antidepressant effect. Similarly, a subject who does not carry a Tph2 variant and/or low serotonin levels may be administered 5-HTP to boost the effects of a serotonin enhancer on endogenous extracellular serotonin levels in the brain, which may aid in treatment with a small risk of side effects.

The term "SSRI" or "selective serotonin-inhibitor" refers to those compounds typically used as antidepressants and are associated with the increase in the extracellular level of the neurotransmitter serotonin by inhibiting its uptake into the presynaptic cell, increasing the level of serotonin in the synaptic cleft available to bind to the postsynaptic receptor. Example of suitable SSRIs include, but are not limited to, citalopram, dapoxetine, escitalopram, fluoxetine, fluvoxamine, indalpine, paroxetine, sertraline, vilazodone, zimelidine and combinations thereof. In some embodiments, the SSRI is fluoxetine.

Numerous serotonin enhancers and serotonin enhancer therapies are known. See, e.g., U.S. Pat. No. 6,218,395. The serotonin enhancer can be a serotonin reuptake inhibitor, for example, a selective serotonin reuptake inhibitor (SSRI), such as described in U.S. Pat. Nos. 6,552,014; 6,492,366; 6,387,956; 6,369,051; or 5,958,429; or U.S. Patent Application Publication Nos. 2010/0267772 to Willigers; 2008/0132514 to Pinney et al.; 2007/0042014 to Cremere et al.; 2003/0191126 to Kodo et al.; or 2002/0103249 to Bogeso et al. (each incorporated herein by reference).

Examples of known serotonin reuptake inhibitors that may be used in carrying out the present invention include, but are not limited to:

cianopramine or a pharmaceutically acceptable salt thereof (e.g., 5-[3-(dimethylamino)propyl]-10.11-dihydro-5H-dibenz[b,f]azepine-3-carbonitrile);

citalopram or a pharmaceutically acceptable salt thereof (e.g., 1-[3-(dimethylamino)propyl]-1-(p-fluorophenyl)-1,3-dihydro-isobenzofuran-5-carbonitrile);

escitalopram or a pharmaceutically acceptable salt thereof (e.g., (S)-1-3-dimethylamino-propyl-1-(4'-fluoro-phenyl)-1,3-dihydro-isobenzofuran-5-carbonitril, oxalate);

dapiprazole or a pharmaceutically acceptable salt thereof (e.g., 5,6,7,8-tetrahydro-3-[2-(4-o-tolyl-1-piperazinyl) ethyl]-1,2,4-triazolo[4,3-a]pyridine (hydrochloride));

desvenlafaxine or a pharmaceutically acceptable salt thereof (e.g., Phenol, 4-[2-(dimethylamino)-1-(1-hydroxycyclohexyl)ethyl]-(Z)-2-butanedioate (1:1) monohydrate);

duloxetine or a pharmaceutically acceptable salt thereof, including LY 223.332, LY264.452 ((−)-enantiomer), LY248.686 (HCl), and Y227.942 (+)-enantiomer) (e.g., (+)-(S)—N-methyl-(1-naphtyloxy)-2-thiophenepropylamine (HCl));

fluoxetine or a pharmaceutically acceptable salt thereof (e.g., 3-[(p-trifluoromethyl)phenoxy]-N-methyl-3-phenyl-propylamine (hydrochloride));

fluvoxamine or a pharmaceutically acceptable salt thereof (e.g., (E)-5-methoxy-4'-(trifluoromethyl)valerophenone O-(2-amino-ethyl)oxime (hydrogen maleate));

ifoxetine or a pharmaceutically acceptable salt thereof (e.g., (+/−)-cis-4-(2,3-xylyoxy)-3-piperidinol (sulfate));

indalpine or a pharmaceutically acceptable salt thereof (e.g., 3-[2-(4-piperidyl)ethyl]indole);

LY 113.821 or a pharmaceutically acceptable salt thereof (e.g., N-methyl-3-(1-naphthoxy)-3-phenylpropylamine);

mirtazapine or a pharmaceutically acceptable salt thereof (e.g., 1,2,3,4,10.14-hexahydro-2 methylpiprazino[2,1-a]pyrido[2,3-c]benzazepine);

nefazodone or a pharmaceutically acceptable salt thereof (e.g., 1-[3-[4-(m-chlorophenyl)-1-piperazinyl]propyl]-3-ethyl-4-(2-phenoxyethyl)-$^2$-1,2,4-triazolin-5-one (HCl));

2-nitroimipramine or a pharmaceutically acceptable salt thereof (e.g., 5-[3-(dimethylamino)propyl]-2-nitro-10.11-dihydro-5H-dibenz[b,f]azepine (hydrochloride);

nortriptyline or a pharmaceutically acceptable salt thereof (e.g., 10.11-dihydro-N-methyl-5H-dibenzo[a,d]cycloheptene-$\Delta^{5,\Gamma}$propylamine (hydrochloride));

paroxetine or a pharmaceutically acceptable salt thereof (e.g., (3S-trans)-3-[(1,3-benzodioxol-5-yloxy)methyl]-4-(4-fluorophenyl)piperidine));

RU 25.591 or a pharmaceutically acceptable salt thereof (e.g., cis-6,7,8,9-tetrahydro-N,N-dimethyl-5-(p-nitrophenoxy)-5H-benzocyclohepten-7-amine (fumarate));

sercloremine or a pharmaceutically acceptable salt thereof (e.g., 4-(5-chloro-2-benzofuranyl)-1-methylpiperidine (hydrochloride));

sertraline or a pharmaceutically acceptable salt thereof (e.g., (+)-cis(1S,4S)-4-(3,4-dichlorophenyl)-1,2,3,4-tetrahydro-N-methyl-1-naphthylamine (HCl));

setiptiline or a pharmaceutically acceptable salt thereof (e.g., 2,3,4,9-tetrahydro-2-methyl-1H-dibenzo[c,f]cyclohepta[1,2-c]pyridine (maleate));

tianeptine or a pharmaceutically acceptable salt thereof (e.g., N-(3-chloro-6,11-dihydro-6-methyldibenzo[c,f] [1,2]thiazepin-11-yl)-7-amino-heptanoic acid S,S-dioxide);

trazodone or a pharmaceutically acceptable salt thereof (e.g., 2-[3-[4-(3-chlorophenyl)-1-piperazinyl]propyl]-1,2,4-triazolo[4,3-a]pyridin-3(2H)-one (hydrochloride));

venlafaxine or a pharmaceutically acceptable salt thereof (e.g., (+/−)-1-[2-(dimethylamino)-1-(p-methoxyphenyl)ethyl]cyclohexan-1-ol (HCl))

viqualine or a pharmaceutically acceptable salt thereof (e.g., cis-6-methoxy-4-[3-(3R,4R)-(3-vinylpiperidyl) propyl]-quinoline); and zimeldine or a pharmaceutically acceptable salt thereof (e.g., (Z)-3-(p-bromophenyl)-N,N-dimethyl-3-(3-pyridyl)allylamine).

The serotonin enhancer can be a monoamine oxidase inhibitor (MAOI) such as described in U.S. Pat. Nos. 6,472,423 and 6,011,054. Examples of monoamine oxidase inhibitors include, but are not limited, to isocarboxazid, phenelzine, tranylcypromine, and phenethylamines such as selegiline. The serotonin enhancer can be a serotonin agonist such as described in U.S. Pat. Nos. 6,656,172; 6,579,899 and 6,387,907. The serotonin enhancer can be an amphetamine, including, but not limited to, derivatives thereof such as phentermine, fenfluramine, and (+)-3,4-methylenedioxyamphetamine. The serotonin enhancer can be a tricyclic antidepressant such as described in U.S. Pat. Nos. 6,368,814; 6,358,944; 6,239,162; and 6,211,171. Examples of tricyclic antidepressants include, but are not limited to, imipramine, amitriptyline and clomipramine.

The serotonin enhancer can be an anxiolytic such as buspirone or ipsapirone.

The serotonin enhancer can be a precursor or prodrug of serotonin, or an intermediate in serotonin biosynthesis, such as described in U.S. Pat. Nos. 6,579,899; 6,013,622; and 5,595,772. Examples include tryptophan, 5-hydroxytryptophan (5-HTP), TPH2 co-factor tetrahydrobiopterin and its precursors, and a tryptophan-rich diet or dietary supplements of tryptophan.

The enzymatic cofactor tetrahydrobiopterin [(6R)-L-erythro-5,6,7,8-tetrahydrobiopterin (or "BH4") may also be administered according to some embodiments. See, e.g., U.S. Pat. Nos. 6,451,788 and 4,920,122. While the present invention is described primarily with reference to BH4, other BH4 enhancers such as folates and analogs thereof, (e.g., methylfolate) as well as estrogen agonists and glucocorticoid antagonists may be used in addition, or in alternative, thereto. Folate analogs are known and described in, for example, U.S. Pat. Nos. 6,808,725; 6,673,381; 6,500,829; and 6,191,133.

Vitamin B6, which is a cofactor in the conversion of 5-HTP to serotonin in the body, may also be administered, as desired.

Formulations may be provided in any suitable form, such as tablets, capsules, suppositories, inhalation or aerosolizable formulations, formulations in an inhalation delivery device, parenterally injectable formulations, etc. In the case of a neutraceutical composition, the formulation may be provided in the form of a bar, beverage, drink, snack food, etc.

The active compounds may be administered to the subject by any suitable route, including oral administration, buccal administration, parenteral injection, inhalation or aerosol administration, transcutaneous administration, etc.

The therapeutically effective dosage of any specific active compound, the use of which is in the scope of present invention, will vary somewhat from compound to compound, and patient to patient, and will depend upon the condition of the patient and the route of delivery.

For example, a serotonin enhancer such as a serotonin reuptake inhibitor can be administered to the average adult human for the treatment of the disorders described herein in an amount of from about 0.1 mg to about 2000 mg, preferably from about 1 mg to about 200 mg per unit dose.

A peripheral decarboxylase inhibitor such as carbidopa, benserazide or methyldopa can, in some embodiments, be administered to an average adult human subject in an amount of from 5 or 10 to 25, 50 or 100 milligrams per unit dose in combination with the 5-HTP.

A precursor or prodrug of serotonin, or an intermediate in serotonin biosynthesis, including 5-hydroxytryptophan (5-HTP), may be administered in an amount of from about 1, 2, 5 or 10 milligrams up to 0.1, 0.5, 1 or 4 grams per unit dose.

The therapeutically effective dosage may also vary depending upon whether two or more agents are administered in combination. For example, while 5-HTP alone may have only a modest effect on depression, 5-HTP in combination with a serotonin enhancer such as an SSRI may have a potent synergistic effect, yielding a larger increase in extracellular 5-HT as compared to the addition of the SSRI and 5-HTP effects. Therefore, a therapeutically effective dosage of 5-HTP when administered in combination with an SSRI may in some embodiments be lower that a therapeutically effective dosage of 5-HTP alone. In addition, administration of a slow-release 5-HTP may result is a different dosage (e.g., a lower dose, or higher dose to be released over a longer period of time) than would be effective as an immediate-release formulation. Administration of unit doses of active agents, alone or in combination, may be one or several times daily, for example 2, 3, 4 or 8 times, giving for example, 1, 2 or 3 doses each time.

As used herein, the administration of two or more agents (inclusive of serotonin enhancers) "in combination" means that the agents are applied closely enough in time that the presence of one alters the biological effects of the other. The two agents may be applied simultaneously (concurrently or contemporaneous) or sequentially. Administrations according to some embodiments may be within a period of time that ranges from minutes (e.g., 1, 5, 10, 30, 60, or 90 minutes or more) to days (e.g., 1, 2, 5, 8 or 10 or more days), as appropriate for efficacious treatment.

Simultaneous, concurrent or contemporaneous administration of the agents may be carried out by mixing the agents prior to administration, or by administering the agents at the same point in time but different routes of administration, or applied at times sufficiently close that the results observed are indistinguishable from those achieved when the compounds are applied at the same point in time.

Sequential administration of the agents may be carried out by administering one agent at some point in time prior to administration of a second agent, such that the prior administration of one alters or enhances the effects of the other, or vice versa.

"Enhance the activity of" as used herein means the agent (a) increases the treatment efficacy of an otherwise efficacious agent to an even more efficacious level; or (b) increases the treatment efficacy of an otherwise ineffective active agent to an efficacious level.

Biomarkers may also be detected and/or monitored as appropriate or desired, and may be used to detect an imbalance in monoamine neurotransmitters such as serotonin, catecholamines (e.g., dopamine, epinephrine and norepinephrine), etc. Biomarkers can be measure in a biological sample such as blood, cerebrospinal fluid (CSF), or urine. These biomarkers include, but are not limited to, metabolites such as 5-HIAA, homovanillic acid, and vanillylmandelic acid. For example, decreased cerebrospinal fluid (CSF) levels of 5-hydroxyindoleacetic acid (5-HIAA), the main metabolite of serotonin, may be measured and/or monitored to probe serotonin levels in the body. Detection of elevated 5-HIAA (and, optionally, detection of low homovanillic acid and/or vanillylmandelic acid) may indicate a neurochemical imbalance due to elevated serotonin. Such elevated serotonin may contraindicate treatment with a serotonin enhancer such as an SSRI and/or 5-HTP. Homovanillic acid is a catecholamine metabolite and is associated with dopamine levels in the brain. Similarly, vanillylmandelic acid is a metabolite of the catecholamines epinephrine and norepinephrine.

Altered 5-HT receptor responses are known to be associated with depression and suicidality, e.g. 15-$HT_{2A}$, 15-$HT_{1A}$. Hypothermic responses to 5-HT receptor agonists (e.g., 5-$HT_{1A}$ receptor agonists) may also be measured and/or monitored as known in the art. For example, measurement of the hypothermic response in response to 5-$HT_{1A}$ receptor agonists is known. See, e.g., Rausch et al., "Temperature Regulation in Depression: Functional 5HT1A Receptor Adaptation Differentiates Antidepressant Response, Neuropsychopharmacology, 2006, 31:2274-2280. Examples of 5-HT$_{1A}$ receptor agonists include, but are not limited to, 8-OH-DPAT, alnespirone, AP-521, buspar, buspirone, dippropyl-5-CT, DU-125530, E6265, ebalzotan, eptapirone, flesinoxan, flibanserin, gepirone, ipsapirone, lesopitron, LY293284, LY301317, MKC242, R(+)-UH-301, repinotan, SR57746A, sunepitron, SUN-N4057, tandosporine, U-92016A, urapidil, VML-670, WAY-100635, zalospirone or zaprasidone.

Decreased prolactin or cortisol response to a 5-HT releaser (e.g., fenfluramine) may also be measured, as desired. Other signs or symptoms which may be considered and/or monitored include the presence of normal working memory but deficits in recognition and recall memory, which are known to be associated with serotonin dysregulation disorders such as depression in humans.

The present invention is explained in greater detail in the following non-limiting Examples.

Example 1

The effect of 5-HTP administration was tested in wild-type and 5-HT deficient Tph2KI (R439H) mice. Administration of 5-HTP by providing 5-HTP in drinking water (4 mg/ml≈320 mg/kg/day, no carbidopa) robustly restored brain 5-HT in 5-HT deficient mice towards normal (FIG. 1).

Figure 2A:
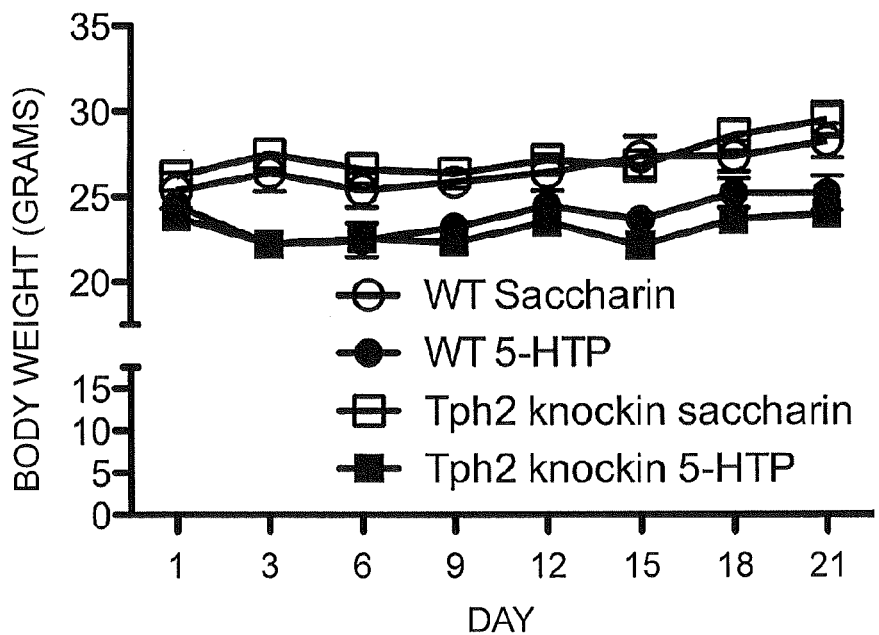
Figure 2B:
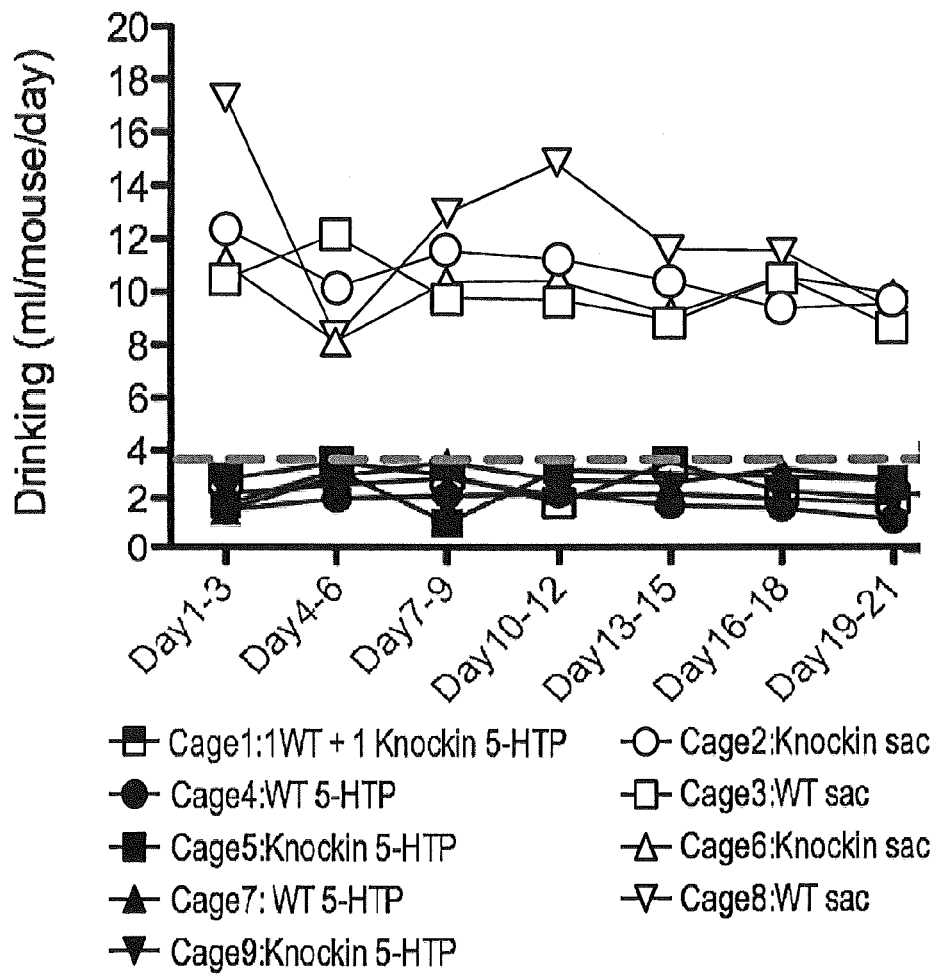
Figure 3A:
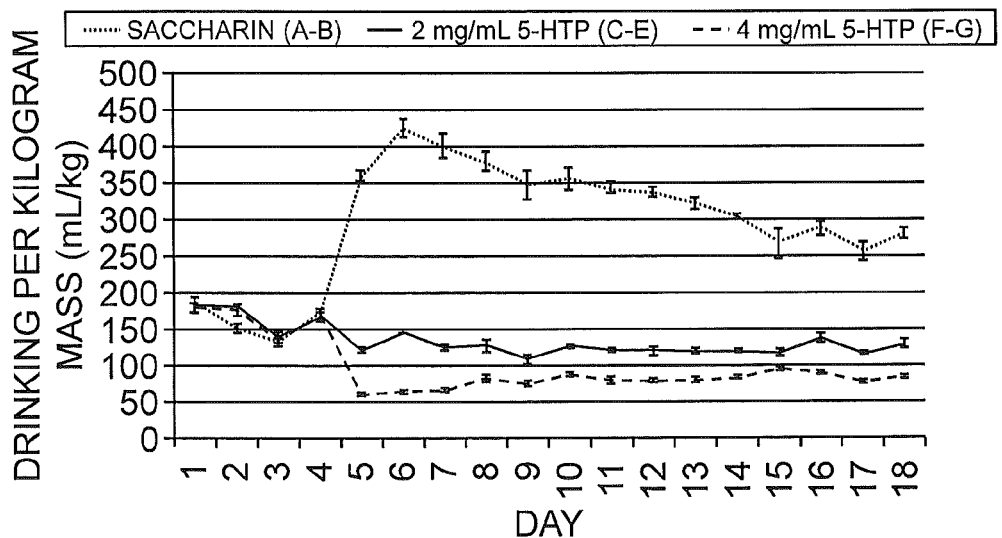
FIGS. 3A-3C. Decreased drinking observed coincides with the body weight decrease observed after 5-HTP administered at 2 mg/ml and 4 mg/ml.
Figure 3B:
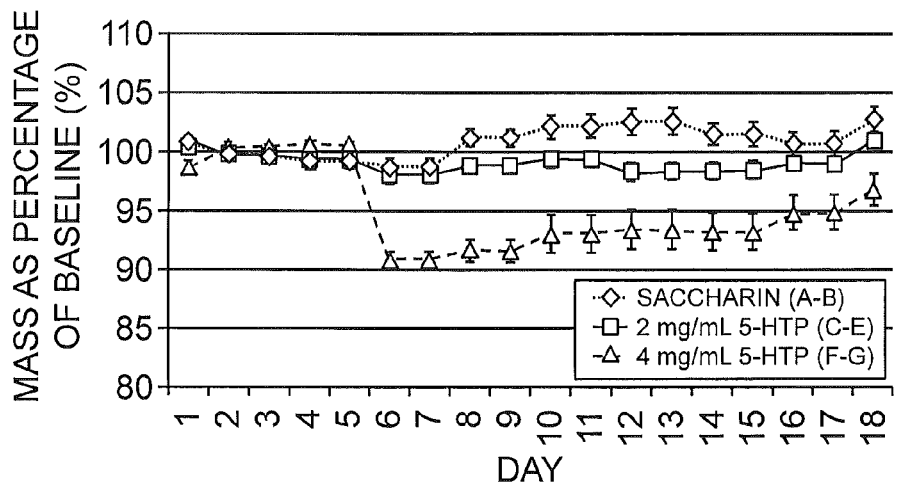
Figure 3C:
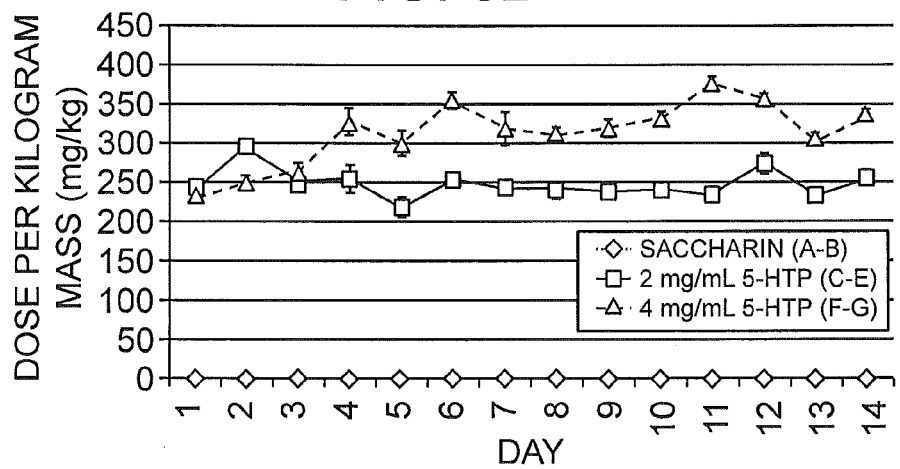

There was a body weight decrease observed after 5-HTP 4 mg/ml (FIG. 2), but it seems to be related to decreased drinking (FIG. 3). No diarrhea and no obvious malaise were observed (data not shown).

Figure 4:
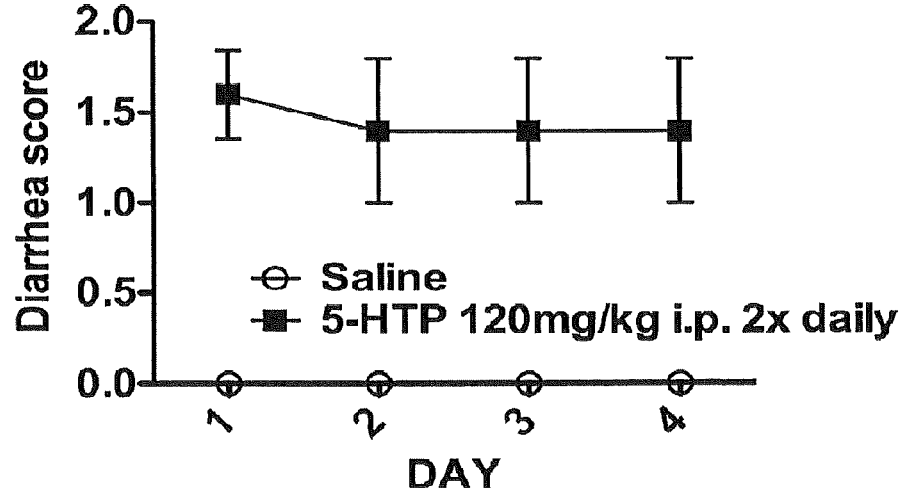
FIG. 4. Administration by bolus injection of 5-HTP 120 mg/kg i.p. caused diarrhea and obvious malaise. A score of 0=absence; 1=trace; and 2=obvious/severe.

Bolus injection of 5-HTP 120 mg/kg i.p., however, caused diarrhea (FIG. 4) and obvious malaise (data not shown).

Figure 5A:
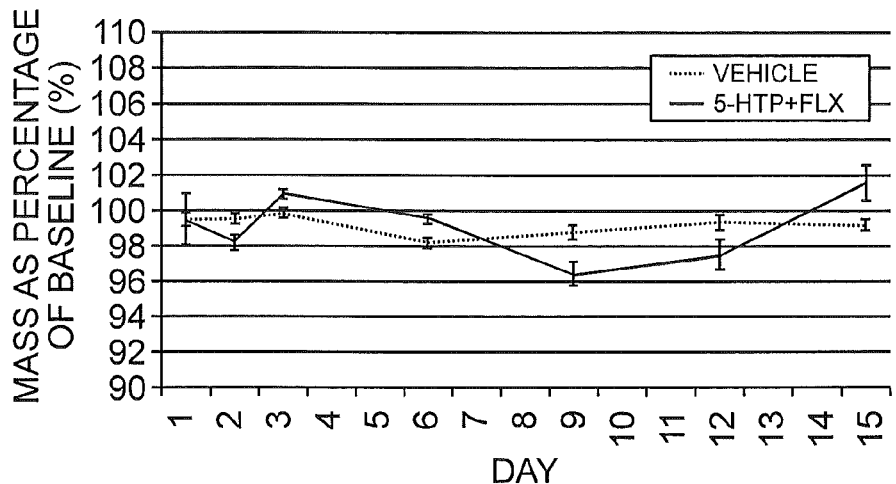
FIGS. 5A-5C. No toxicity was observed as reflected by weights (5A, 5B), head twitches and diarrhea (not shown), upon administration of oral 5-HTP (≈200 mg/kg/day (5C), no carbidopa) as an add-on to existing Fluoxetine (≈18 mg/kg/day (5C)).
Figure 5B:
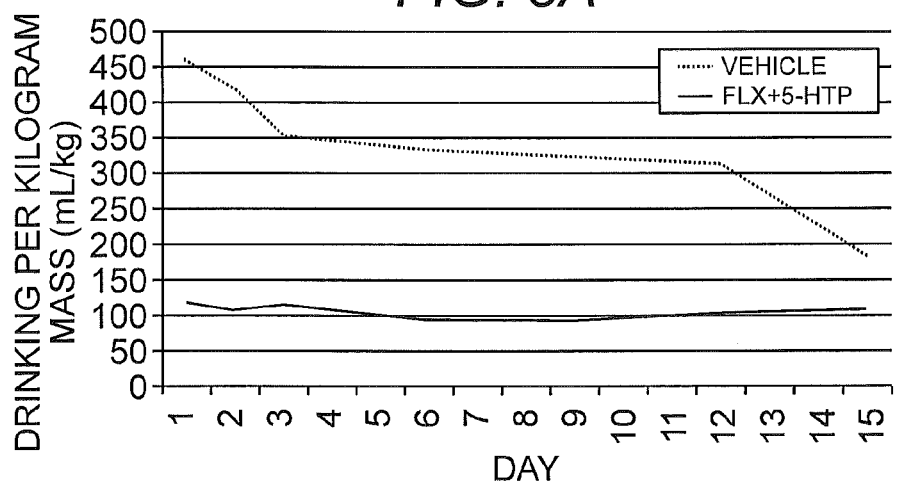
Figure 5C:
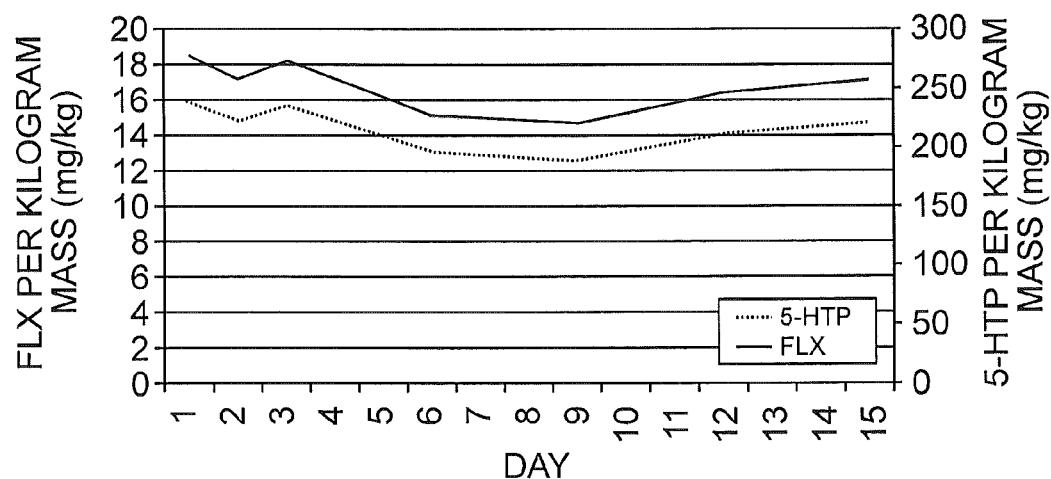

Administration of 5-HTP as an adjunct to serotonin enhancer administration was also tested by using (≈200 mg/kg/day) 5-HTP as an add-on to existing chronic fluoxetine administration (≈18 mg/kg/day). No indication of toxicity was observed (weights, head twitches, diarrhea) (FIG. 5), illustrating the feasibility of adding on 5-HTP slow-release to existing SSRI treatment.

Figure 6A:
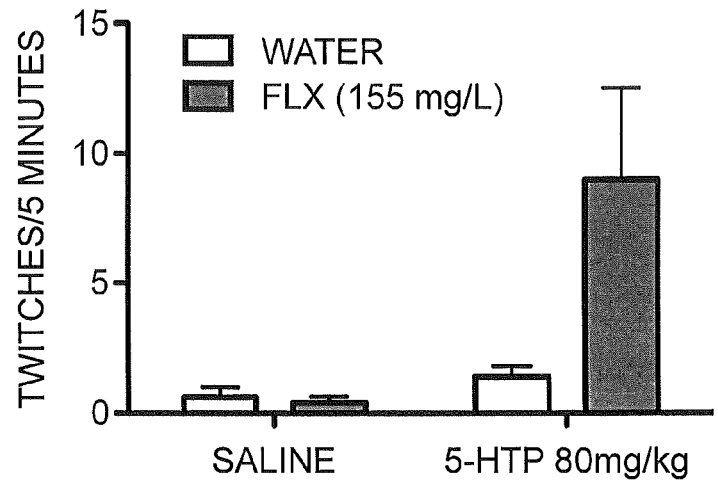
FIGS. 6A-6B. Serotonin syndrome-like behavior was observed upon administration of an acute 5-HTP bolus (80 mg/kg, i.p.) as an add-on to existing Fluoxetine (FLX) (≈18 mg/kg/day) (6A, 6B). However, FLX unexpectedly appeared to lessen 5-HTP-induced diarrhea when assessed by scoring the presence of peri-rectal fecal smearing (6B).
Figure 6B:
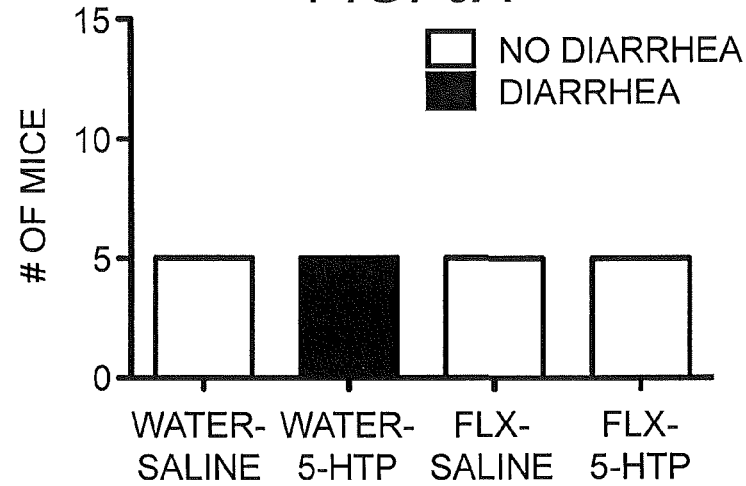

In contrast, administration of an acute 5-HTP bolus (80 mg/kg, i.p.) as an add-on to existing fluoxetine (FLX) (≈18 mg/kg/day) resulted in 5-HT syndrome-like behavior (FIG. 6). However, FLX unexpectedly seems to decrease diarrhea induced by 5-HTP (FIG. 6), although not rigorously tested in this experiment.

In summary, it was found that continuous oral, high-dose 5-HTP restores tissue 5-HT levels under conditions of 5-HT deficiency. Carbidopa was not necessary for the effect.

Bolus 5-HTP administration caused gastrointestinal side effects in the mice. Continuous 5-HTP administration, however, did not result in gastrointestinal side effects.

These data on coadministration of continuous/slow-release 5-HTP as an add-on to FLX indicates that this combination is not toxic and does not result in side effects. This finding contrast to common beliefs among individuals skilled in the art, the laity and recommendations from government agencies, i.e. NIMH. Bolus/immediate release 5-HTP, however, causes 5-HT syndrome in FLX-treated mice.

Example 2

Potentially, selective serotonin reuptake inhibitor (SSRI) effects on extracellular serotonin (5-HT$_{Ext}$), and hence the clinical effect, could be enhanced by co-administration of 5-HTP (the immediate precursor of 5-HT). This could particularly apply to, but not be restricted to, patients with low endogenous brain 5-HT, for instance caused by decreased brain Tph2 catalytic function. 5-HTP per se may have poor drugability, however. 5-HTP has fast-in-fast-out kinetics, often causing side-effects upon ingestion even at moderate doses (e.g., gastro-intestinal disturbances, dizziness) and short time of action (Gijsman et al., Placebo-controlled comparison of three dose-regimens of 5-hydroxytryptophan challenge test in healthy volunteers, *J Clin Psychopharmacol* 22, 183 (April, 2002); Lowe et al., L-5-Hydroxytryptophan augments the neuroendocrine response to a SSRI. *Psychoneuroendocrinology* 31, 473 (May, 2006). Thus, 5-HTP as augmentation for SSRIs could be associated with cycling between side-effects/overdose and drug-withdrawal as well as suboptimal overall exposure.

However, administering 5-HTP as a slow release (SR) formulation could ameliorate 5-HTP's poor drugability by i) decreasing absorption rate; ii) decreasing peak levels, iii) prolonging exposure time, iv) enhancing total exposure and v) facilitating patient compliance. Thus, formulating 5-HTP as an SR formulating could transform 5-HTP into a more clinically useful medication and greatly improve 5-HTP's therapeutic potential.

In this study, the potential of add-on of 5-HTP SR to augment the 5-HT$_{Ext}$ response to chronic fluoxetine (FLX, an SSRI) was assessed in Tph2 R439H mice, a naturalistic and clinically relevant model of endogenous 5-HT deficiency (Jacobsen et al., Deficient serotonin neurotransmission and depression-like serotonin biomarker alterations in tryptophan hydroxylase 2 (Tph2) loss-of-function mice. *Molecular Psychiatry* (May 3, 2011); Beaulieu et al., Role of GSK3 beta in behavioral abnormalities induced by serotonin deficiency. *Proceedings of the National Academy of Sciences of the United States of America* 105, 1333 (2008)).

Methods

Experiment #1

Wild type and Tph2 R439H mice were treated for >3 wks with a saturating dose of FLX (155 mg/L drinking water, ~20 mg/kg/day) or left untreated (water) and 5-HT microdialysis was performed as described in Jacobsen, J P R et al, (Deficient serotonin neurotransmission and depression-like serotonin biomarker alterations in tryptophan hydroxylase 2 (Tph2) loss-of-function mice. *Molecular Psychiatry* (May 3, 2011)). Briefly:

Materials:

Escitalopram was a generous gift from Lundbeck (Valby, Denmark). Dexfenfluramine, 8-OH-DPAT, DOI, 5-HT, 5-hydroxytryptophan (5-HTP), 5-HIAA, 3,4-dihydroxyphenylacetic acid, homovanillic acid and clonidine were purchased from Sigma (St. Louis, Mo., USA). NAN-190 and DPCPX were purchased from Tocris (Ellisville, Mo., USA). [$^{125}$I]p-MPPI was obtained from Perkin Elmer (Waltham, Mass., USA). [$^{3}$H]WAY100635, [$^{3}$H]ketanserin, [$^{3}$H]citalopram and [$^{35}$S]GTPγS were purchased from Perkin Elmer. All other reagents used were of analytic grade. All drugs were administered in a volume of 10 ml kg$^{-1}$ in saline, intraperitoneal (i.p.) or subcutaneous (s.c.), as indicated.

Microdialysis:

Mice were anesthetized by ketamine/xylazine (100 and 10 mg kg$^{-1}$, respectively, in saline, i.p) and a guide cannula (CMA7, CMA Microdialysis, Chelmsford, Mass., USA) was stereotactically implanted into the frontal cortex (AP: 2.3 mm, ML: 0.3 mm, DV: 0.7 mm), hippocampus (AP: −3.3 mm, ML: 3.0 mm, DV: 1.5 mm) or lateral ventricle (AP: 0.3 mm; ML: 0.9 mm; DV: 2.0 mm) according to the atlas by Franklin and Paxinos (see, e.g., Franklin, K. and Paxinos, G. *The Mouse Brain in Stereotaxic Coordinates*. Academic Press: San Diego, 1997) and fixed in place with two anchor screws (CMA) and carboxylate dental cement (CMA). Operated mice were singly housed, treated with antibiotics (1.2 mg sulfamethoxazole ml$^{-1}$ and 0.24 mg trimethoprim ml$^{-1}$) in the drinking water and allowed to recover 48-96 h post-surgery.

Dialysate Collection:

The microdialysis probe was inserted into the guide cannula approximately 16 h before the start of sample collection to allow for the stabilization of 5-HT$_{Ext}$ levels. It has been previously demonstrated that dialysate analyte levels are usually only influenced by the tissue trauma caused by probe insertion for a few hours and that the blood-brain barrier is usually not compromised in brain microdialysate experiments (Chaurasia, C S et al. (2007) *J Clin. Pharmacol.* 47:589-603). However, we employed a relatively long (overnight) stabilization period to ensure that we reached stable baseline 5-HT$_{Ext}$ levels unaffected by peripheral (that is, Tph1 derived) 5-HT. In confirmation of the neuronal origin of the dialysate 5-HT, the 5-HT$_{1A}$R agonist 8-OH-DPAT (1 mg kg$^{-1}$, i.p.) decreased 5-HT$_{Ext}$ by approximately 50%, a decrement that is within the range typically reported after 8-OH-DPAT administration (Li, Q. et al. (1999) *J. Pharmacol Exp Ther* 291:999-1007; Rossi, D. et al. (2008) *J Neurochem* 105:1091-1099). The mouse was gently restrained and the microdialysis probe (CMA7 7/2 for frontal cortex and hippocampus, CMA7 7/1 for lateral ventricle) was inserted into the guide cannula. The mouse was then placed in a circular chamber with bedding, chow and water available. A two-channel swivel (cat. no. 375/D/22QM; Instech, Plymouth Meeting, Pa., USA) allowed for unimpeded movement of the mouse. Artificial CSF (147 mM NaCl, 2.7 mM KCl, 0.85 mM MgCl$_2$, 1.2 mM CaCl$_2$, CMA) was delivered at a flow rate of 0.45 μl min$^{-1}$ from probe insertion until the end of experiment. Following the stabilization period, samples (30- or 120-min sample duration, as noted) were collected on ice in the dark, immediately frozen on dry ice and stored at −80° C. Dialysates were analyzed off-line by high-performance liquid chromatography-electrochemical detection (HPLC-EC) for 5-HT, 5-HIAA, 3,4-dihydroxyphenylacetic acid and homovanillic acid, or by the SymDAQ HPLC-tandem-mass spectrometry technology for simultaneous determination of monoamines and amino acids.

Tissue 5-HT Analysis:

Frontal cortex and hippocampus were rapidly dissected and frozen on dry ice. Tissues were homogenized by sonication in 20 volumes of ice-cold 100 mM HClO$_4$. The supernatants were recovered and passed through 0.2 μm filters and 5-HT quantified in the filtrates by HPLC-EC.

Experiment #2

Tph2 R439H mice (~25 g) were treated for >3 wks with a saturating dose of FLX (155 mg/L drinking water, ~20 mg/kg/day). Thereafter Alzet 2001 minipumps (1 μl solvent delivered/hr) containing a 5-HTP solution (100 mg/ml, ~100 mg/kg/day) or only vehicle was implanted (scc.) and 5-HT microdialysis performed at day 5 after pump-implantation. Minipumps deliver a constant flow of solvent from a reservoir and hence mimic the effect of an SR formulation.

Experiment #3

Tph2 R439H mice (~25 g) were treated for >3 wks with a saturating dose of FLX (155 mg/L drinking water, ~20 mg/kg/day). Thereafter Alzet 2001 minipumps (1 μl delivered/hr) containing a 5-HTP solution (100 mg/ml, ~100 mg/kg/day) or only vehicle was implanted using isoflurane anesthesia, allowing for swift awakening, and the mice monitored for signs of 5-HT syndrome hourly for 8 hrs and at 24 hrs. Splaying (0=absent, 1=present, 2=severe), head twitch (#/min) and signs of hyperventilation (0=absent, 1=present, 2=severe) was scored. Body weights—a general index of toxicity—were followed for 2 days prior to and 5 days after pump implantation.

Results

Experiment #1

WT mice showed a robust increase in 5-HT$_{Ext}$ in response to chronic FLX. As previously reported, Tph2 R439H mice had much lower baseline 5-HT$_{Ext}$, and following FLX the 5-HT$_{Ext}$ levels were only enhanced to levels slightly below baseline levels in WT mice (FIG. 7).

Experiment #2

Figure 7:
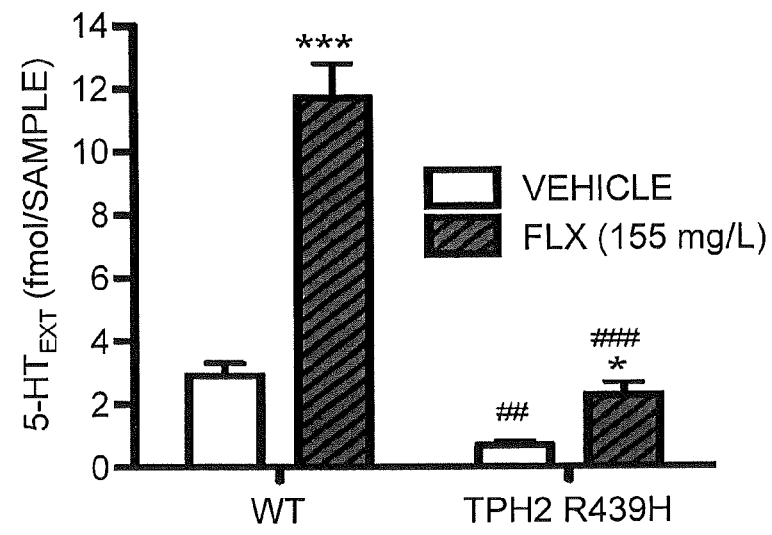
FIG. 7. Wild-type mice showed a robust increase in extracellular serotonin levels (5-HT$_{Ext}$) in response to chronic FLX (≈18 mg/kg/day). Tph2 R439H mice had much lower baseline 5-HT$_{Ext}$, and following FLX the 5-HT$_{Ext}$ levels were only enhanced to levels slightly below baseline levels in WT mice.
Figure 8:
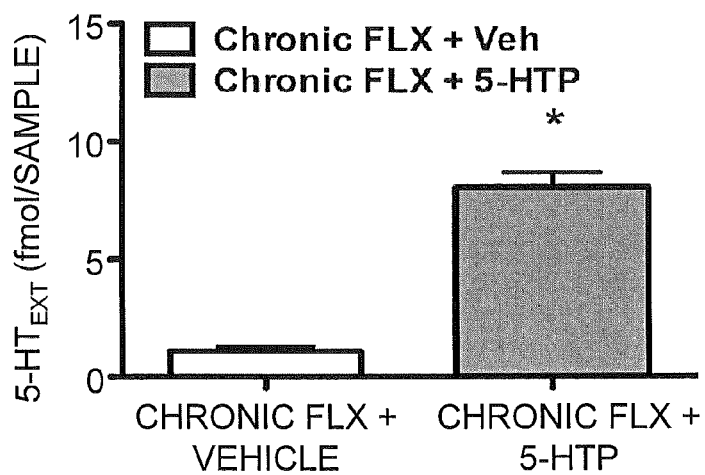
FIG. 8. Five days add-on of 5-HTP SR (~100 mg/kg/day) to chronic FLX (≈18 mg/kg/day) in Tph2 R439H mice produced an 8-fold increase in 5-HT$_{Ext}$, as compared to FLX+vehicle treated mice, bringing the 5-HT$_{Ext}$ close to levels seen in FLX treated WT mice.

Five days add-on of 5-HTP SR in the delivered dose (~100 mg/kg/day) to chronic FLX in Tph2 R439H mice produced a 8-fold increase in 5-HT$_{Ext}$, as compared to FLX+vehicle treated mice (FIG. 8), bringing the 5-HT$_{Ext}$ close to levels seen in FLX treated WT mice (FIG. 7).

Experiment #3

Figure 9A:
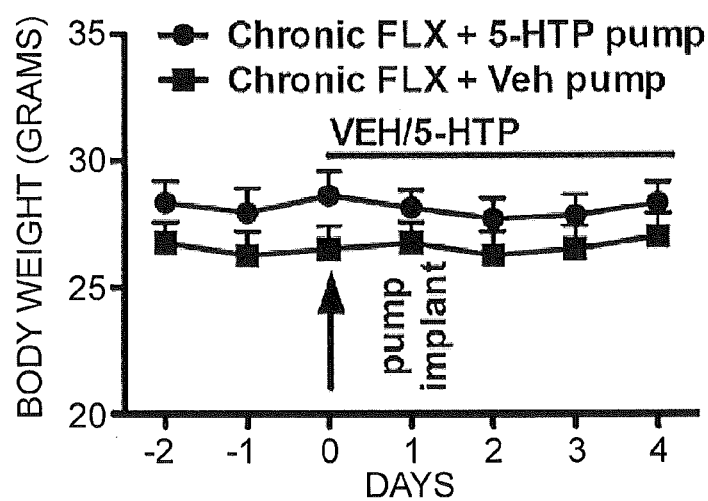
FIGS. 9A-9B. 5-HTP SR in the delivered dose (~100 mg/kg/day) added on to chronic FLX (≈18 mg/kg/day) in WT mice produced no signs of toxicity, i.e. body weight changes of the first 4 days of treatment (9A) or 5-HT syndrome-like behaviors upon treatment initiation (9B).
Figure 9B:
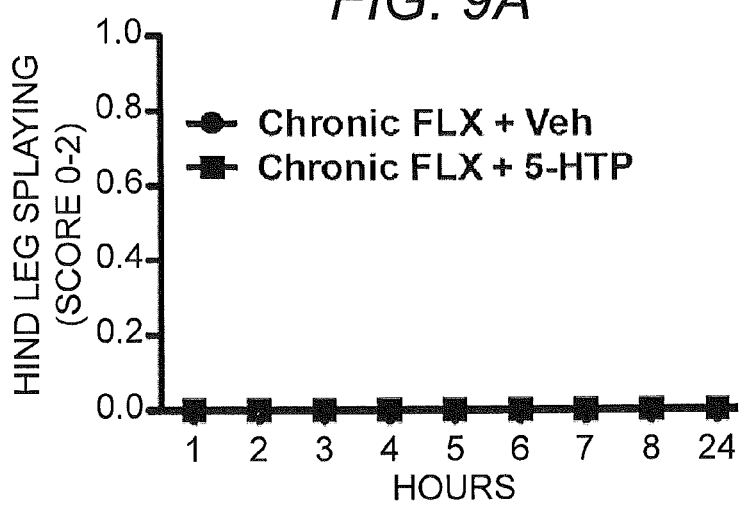
Figure 11A:
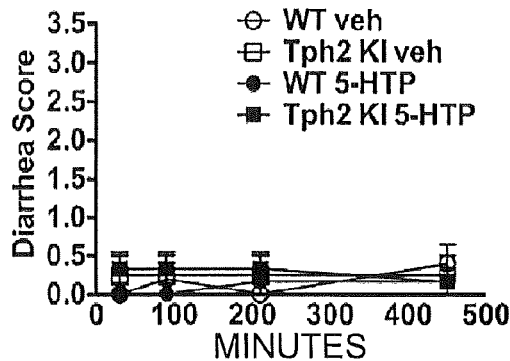
Figure 11B:
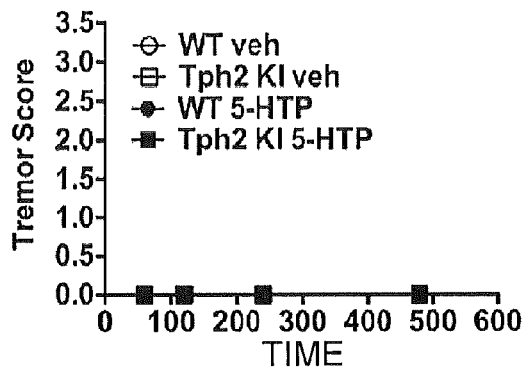
Figure 11C:
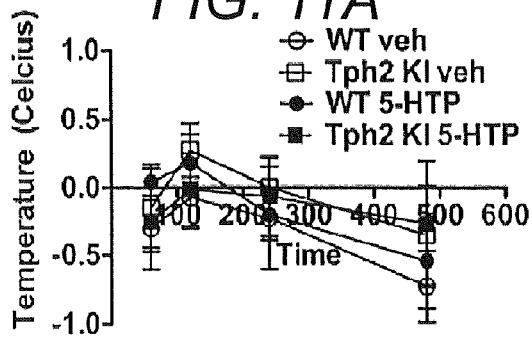
Figure 11D:
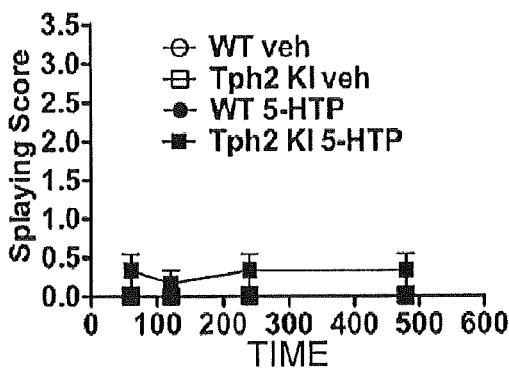
Figure 11E:
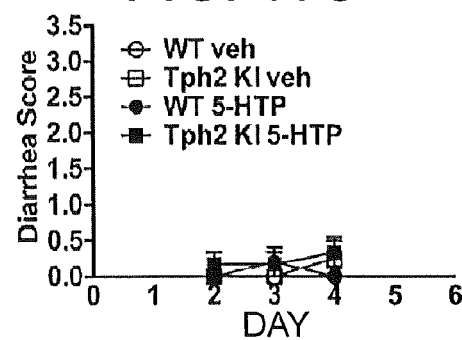
Figure 11F:
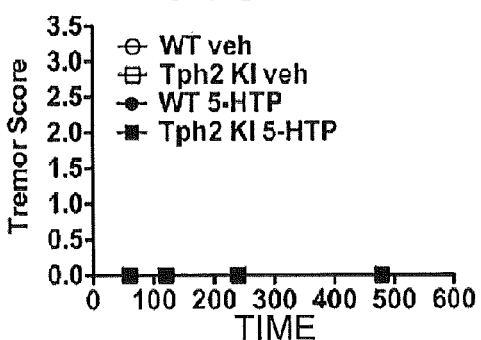
Figure 11G:
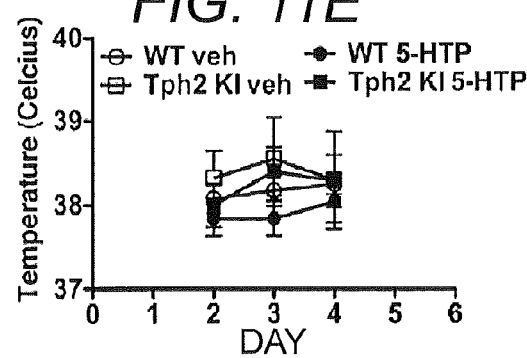
Figure 11H:
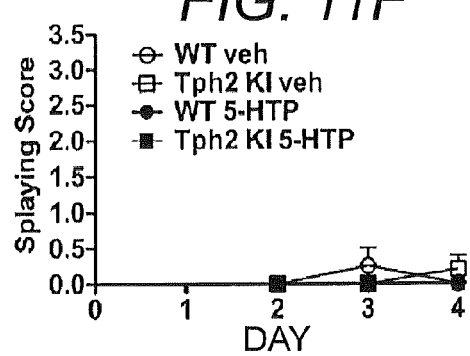
Figure 12E:
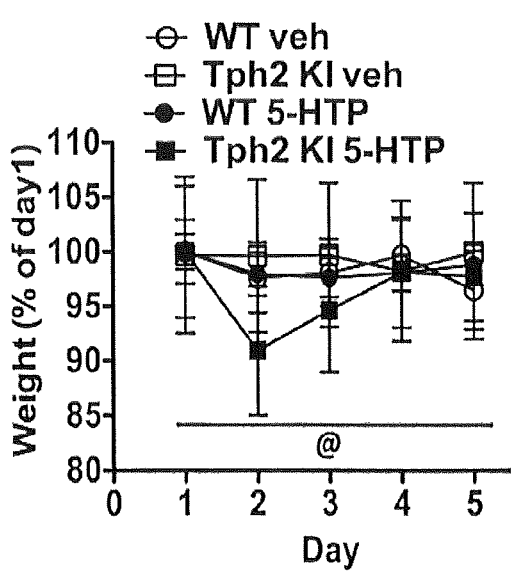
Figure 12F:
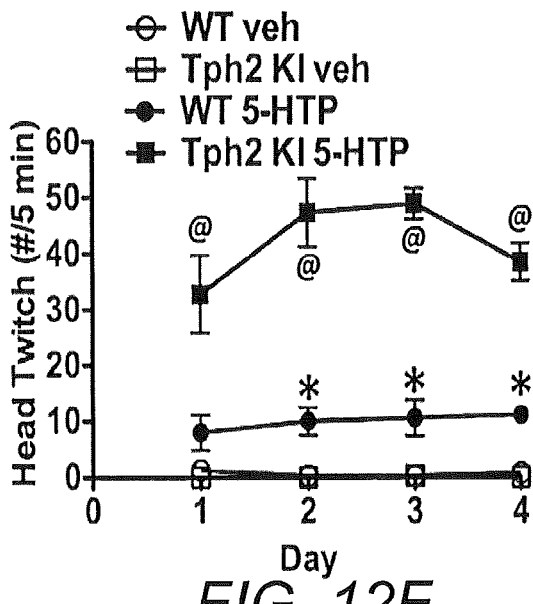
Figure 12G:
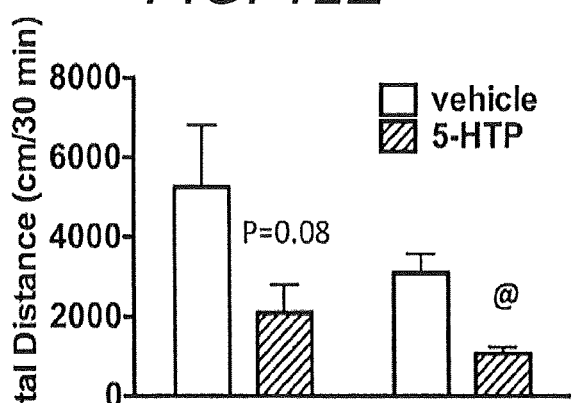
Figure 12H:
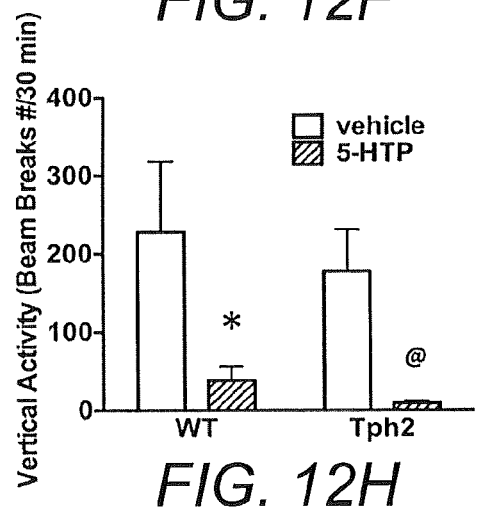
Figure 12I:
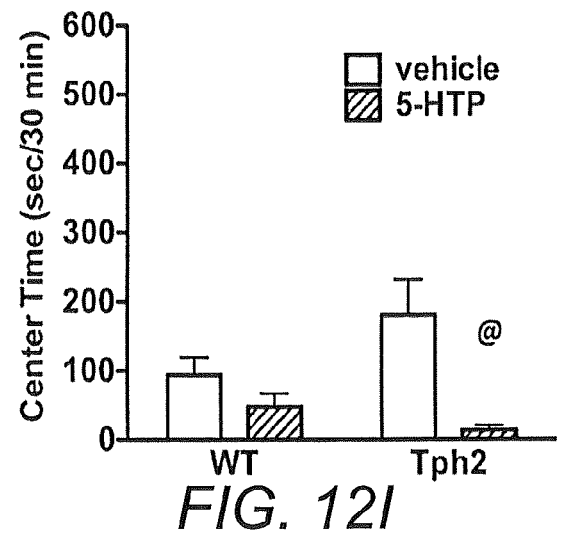
Figure 13A:
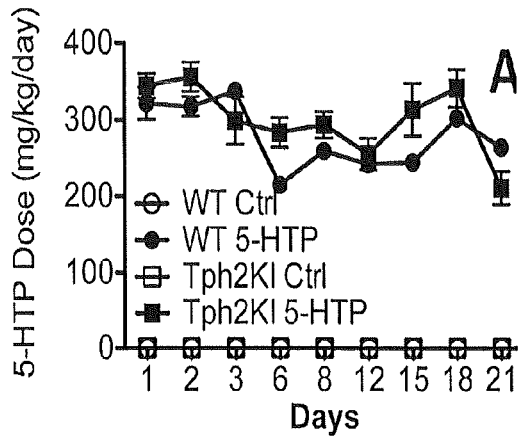
FIGS. 13A-13F. Oral 5-HTP SR (~250 mg/kg/d) increases 5-HT storage in 5-HT deficient Tph2KI mice in the absence of obvious side-effects. 13A: Daily oral 5-HTP dose achieved over 21 days. 13B: No change in body weights during 21 days of oral 5-HTP SR treatment. 13C: Increase in 5-HT storage as measured at noon after 21 days of oral 5-HTP SR treatment. 13D: Increased 5-HIAA (5-HT metabolite) tissue levels as measured at noon after 21 days of oral 5-HTP SR treatment. 13E, 13F: No change in novel open field locomotor activity after 14 days of oral 5-HTP SR treatment. *, p<0.05, WT, ctrl vs 5-HTP, t-test. @, Tph2KI, ctrl vs 5-HTP, t-test.
Figure 13B:
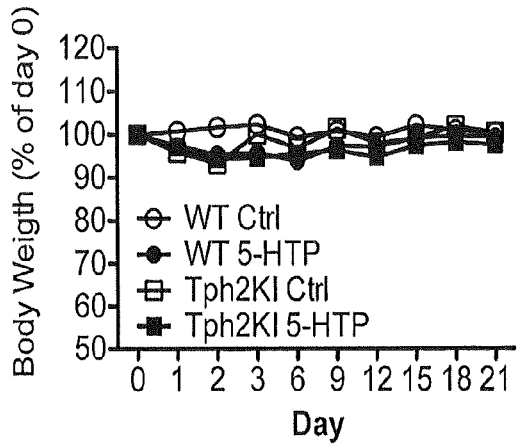
Figure 13C:
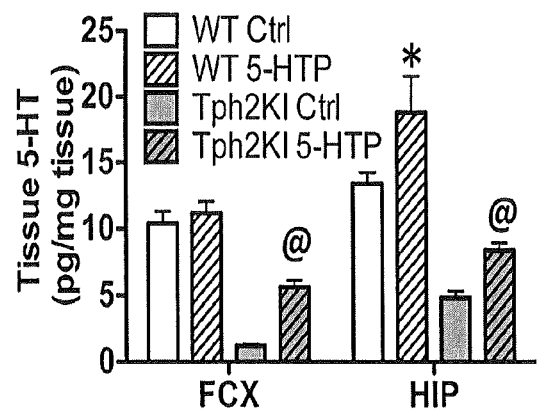
Figure 13D:
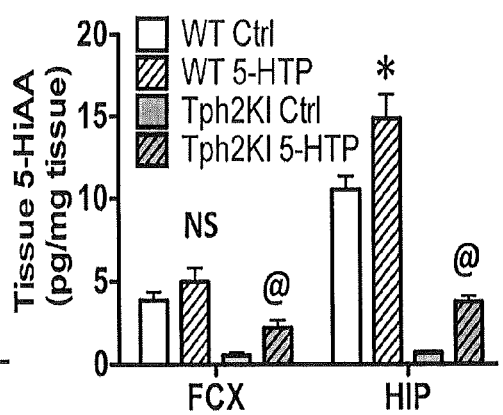
Figure 13E:
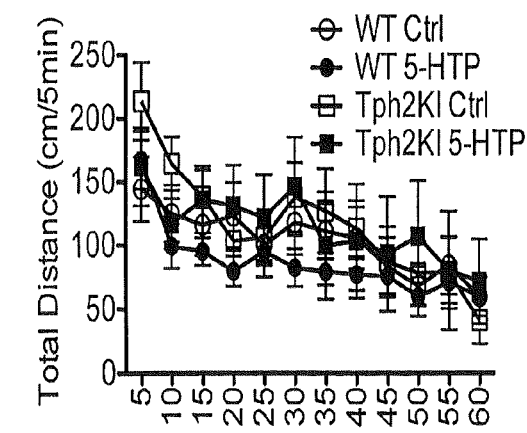
Figure 13F:
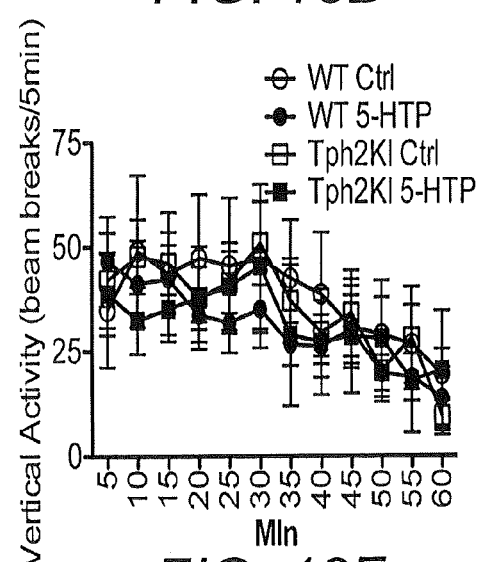

5-HTP SR in the delivered dose (~100 mg/kg/day) produced no signs of toxicity, i.e. body weight changes of the first 4 days of treatment or 5-HT syndrome-like behaviors upon treatment initiation (FIG. 9).

Conclusion. The presented data demonstrate that 5-HTP SR add-on can greatly augment the 5-HT$_{Ext}$ response to chronic SSRI treatment in a mammalian organism harboring a Tph2 enzyme with low catalytic activity, in this case Tph2 R439H. Further, 5-HTP SR add-on in the delivered dose (~100 mg/kg/day) had no discernible toxic effects. Thus, 5-HTP SR add-on to chronic SSRI treatment may represent a viable treatment augmentation strategy in depression and in other diseases related to dysfunction of 5-HT or being treatable with 5-HTergic drugs, such as anxiety, pain and drug abuse.

Example 3

The goal of these studies is to provide a formulation of 5-HTP as a slow-release formulation that will fundamentally improve the drugability of 5-HTP, transforming a natural substance with limited clinical application into an effective drug with wide applicability.

Additional studies showed that 5-HTP SR administered subcutaneously (100 mg/kg/24 h) will boost extracellular serotonin (5-HT) (5-HT$_{Ext}$—the "active" 5-HT) beyond the levels that the SSRI fluoxetine (FLX, prozac) can produce in WT and 5-HT deficient Tph2 R439H mice. This important finding indicates that 5-HTP SR add-on to FLX can boost 5-HT$_{Ext}$ beyond the effect of FLX alone in subjects with normal as well as decreased 5-HT levels (Note differences in y-axis scales).

The subcutaneous minipump mode of delivery applied here emulates well the transdermal mode of administration since 5-HTP in both instances is absorbed via the skin and underlying tissue, bypassing the significant (~50%, (Shindo H et al. Mechanism of intestinal absorption and brain uptake of L-5-hydroxytryptophan in rats, as compared to those of L-3,4-dihydroxyphenylalanine. *Chem Pharm Bull* (Tokyo). June; 25(6):1417-25. (1977))) first-pass metabolism of 5-HTP in the intestine.

As shown in FIG. 10, subcutaneous administration of 5-HTP SR robustly augmented the $5-HT_{Ext}$ response to chronic FLX in WT and 5-HT deficient Tph2KI. These data support 5-HTP SR as an add-on treatment to SSRIs.

Interestingly, while the fold increase was higher in Tph2KI than in WT mice, seven- vs two-fold, the numerical increase was larger in WT mice than in Tph2KI mice, $\Delta 18$ vs $\Delta 6$ fmol/sample. The minipump-approach secures a stable 5-HTP delivery, though the treatment duration is limited to subchronic and the dose by the reservoir size. As is shown in FIG. 11, there was virtually no side-effects associated with the minipump paradigm. Thus, the therapeutic ceiling was not reached, and a stronger 5-HTP SR augmentation of FLX-induced $5-HT_{Ext}$ seems feasible.

Also, 5-HTP SR boosts tissue levels of 5-HT, i.e., "storage" of 5-HT. The 5-HT and 5-HIAA tissue data were collected from mice not treated with FLX because SSRIs per se affects tissue 5-HT and 5-HIAA levels. 5-HTP SR in the applied minipump paradigm robustly increased 5-HT and the metabolite 5-HIAA, as would be expected from the robust effects on $5-HT_{Ext}$. For 5-HTP IR, it was measured 8 h after last injection (total of 9 over 5 days) as a reasonable quasi-approximation for the average 5-HT and 5-HIAA levels administrations.

METHODS: 5-HT Microdialysis 5-HTP SR. $K^+$ depolarization was induced locally by adding 100 mM $K^+$ to the perfusate. A)+B) Mice on >2 w FLX (155 mg/L water, ~20 mg/kg/d) were implanted with Alzet 2001 minipumps (200 ul reservoir) with vehicle (50% DMSO) or 100 mg/ml 5-HTP yielding a hourly (daily) dose of ~4.2(100 mg)/kg for a ~25 g mouse and microdialysis performed at day 5 of vehicle/5-HTP treatment. C) Microdialysis were performed on mice after >2 w FLX. $5-HT_{Ext}$ in dialysates was determined by HPLC-EC. D). Tissue 5-HTP SR: D) Mice were implanted with Alzet 2001 minipumps with vehicle (50% DMSO) or 100 mg/ml 5-HTP yielding a hourly (daily) dose of ~4.2(100 mg)/kg for a ~25 g mouse. On day 5 following pump implantation, the mice were euthanized and tissue collected at 5 PM. Tissue 5-HTP IR: E) Mice were injected AM and PM with 5-HTP SC 50 mg/kg or vehicle (saline) for 4 days. On day 5 only at AM and euthanized 8 h later (5 PM) and tissue collected. Tissue 5-HT and 5-HIAA: HPLC-EC. Statistics: T-test.

Note, the dose of FLX we use is quite high, yielding plasma levels ~10× the clinical, meaning that the serotonin transporter is completely occupied and blocked, and higher doses of FLX alone would not give a higher 5-HText response. Thus, the 5-HTP SR+FLX combo produces higher $5-HT_{Ext}$ than FLX monotreatment appears to be capable of.

Side effects where 5-HTP SR was added to FLX were minimal (FIG. 11). SC 5-HTP SR was well tolerated at the used dose, ~100 mg/kg/d, the same that robustly boosted the $5-HT_{Ext}$ response to chronic FLX. The only significant side effect was a minor and transient weight loss in the Tph2KI mice. Weigh loss is a common effect in rodents of 5-HTergics. Head-twitches could not meaningfully be scored because the presence of the SC pump itself caused twitches. Thus, a regimen of 5-HTP SR add-on to SSRIs that augments the $5-HT_{Ext}$ response (FIG. 10) is associated with virtually no obvious side-effects. The combined data from presented in FIG. 10 and FIG. 11 supports 5-HTP SR as an add-on to SSRIs as an augmentation strategy in disorders treatable with SSRIs such as depression.

METHODS: Mice on >2 w FLX (155 mg/L water, ~20 mg/kg/d) were implanted with Alzet 2001 minipumps with vehicle (50% DMSO) or 100 mg/ml 5-HTP yielding a hourly (daily) dose of ~4.2(100 mg)/kg for a ~25 g mouse. Side-effect parameters were assessed between 30 min and 8 h following pump implantation under brief isoflurane anesthesia (day 1) and then daily (day 2-4). On day 5 mice underwent the open field test. Diarrhea: Mice where placed individually in a cage with filter paper and the diarrhea level scored, 0-3. Tremor and splaying: Scored in home cage from 5 min videos. Temperature: Recorded by digital rectal temperature probe in lightly restrained mice. Open field: The mice were placed in an 40×40 cm open field equipped with photocell panels in three dimensions for 30 min. Center time yields an index of anxiety/agoraphobia. Statistics: Genotypes were analyses separately, with 2way RM-ANOVA or t-test as appropriate, and in the former case followed by Bonferroni post-hoc test.

In contrast, there were marked 5-HT associated side effects upon administration when 5-HTP was given as immediate release (IR) as two daily doses of 50 mg/kg subcutaneously (FIG. 12). SC 5-HTP IR 50 mg/kg/day, the first of two daily doses, was poorly tolerated, causing pronounced 5-HT syndrome-like behaviors. Interestingly, 5-HTP IR appeared to produce more pronounced side-effects in Tph2KI mice for some parameters, i.e., tremor, splaying, head-twitches and open field behaviors, while for diarrhea and hypothermia WT mice seemed more sensitive.

METHODS: Mice on >2 w FLX(155 mg/L water, ~20 mg/kg/day) were injected AM and PM with SC 5-HTP IR (i.e. bolus) 50 mg/kg or vehicle (saline). Side-effects were assessed after the AM dose, day 1-4. Diarrhea: Mice were placed individually in a cage with filter paper and the diarrhea level scored, 0-3, 0-15 min after injection. Tremor, splaying and head-twitch: Scored in home cage from 5 min videos, 25-30 min after injection. Temperature: Recorded by digital rectal temperature probe in lightly restrained mice 30 min after injection. Open field: On day 5, the mice were injected and immediately placed in an 40×40 cm open field equipped with photocell panels in three dimensions for 30 min. Center time yields an index of anxiety/agoraphobia. Statistics: Genotypes were analyzed separately, with 2way RM-ANOVA or t-test where appropriate, and in the former case followed by Bonferroni post-hoc test.

When 5-HTP SR is administered orally (in drinking water), serotonin brain tissue levels are enhanced with no apparent side effects (FIG. 13). This demonstrates that oral 5-HTP reaches the brain and enhances 5-HT levels. Oral 5-HTP SR ~250 mg/kg/day was well tolerated and increased 5-HT storage, robustly in Tph2KI mice, but only minorly in the hippocampus of WT mice. The 5-HT and 5-HIAA augmentation is likely underestimated since mice drink more at night, 5-HTP has a short T½ and tissue was collected at noon. Likely, quite higher doses of 5-HTP could be administered if not for 5-HTP's aversive taste, and higher 5-HTP concentrations inhibited drinking (in pilots). Diarrhea was not specifically scored, but none was noted. Thus, orally ingested 5-HTP will boost brain 5-HT levels, with no apparent side effects.

METHODS: 5-HTP (2 mg/L) was dissolved in (1 mg/L) saccharin-H2O, administered in blackened bottles and changed twice weekly. HPLC pilot experiments demonstrated that 5-HTP was stable for weeks in H2O at RT. Body weights and drinking per cage was followed throughout and 5-HTP consumed estimated here from. Open field: At day 14 all mice were tested for 60 min in a novel open field 40×40 cm for locomotor activity. Tissue 5-HT and 5-HIAA: HPLC-EC.

Example 4

A patient taking a selective serotonin reuptake inhibitor (SSRI) for more than 3-8 weeks, or whatever is deemed necessary by the attending physician to establish insufficient response, is still experiencing symptoms of depression. The patient is administered an oral tablet, or a patch for transdermal administration, of slow-release 5-HTP to take either concurrently with the SSRI, at the same time of day or a different time of the day. The patient is periodically monitored for effectiveness of the treatment and/or the occurrence of side effects.

Dosage of the 5-HTP may be adjusted as deemed appropriate, typically starting with a lower dose, for instance 100-500 mg/day for oral administration on treatment-initiation, and subsequently increased if needed up to several grams per day. For transdermal administration, an example is 25 mg/day to start, and subsequently increased up to 1 gram/day.

Other drugs approved for add-on to SSRIs in depression, i.e. the atypical antipsychotics aripiprazole and quetiapine, appear to work by increasing $5\text{-HT}_{Ext}$ beyond the levels achieved by the SSRI per se. However, slow-release 5-HTP has a distinct mechanism of action, namely increasing the endogenous 5-HT levels available for release, while the atypical antipsychotics rely on existing endogenous 5-HT production. 5-HTP slow-release may, therefore, treat additional segments of depression patients, for instance patients with low endogenous 5-HT production, due for instance to low Tph2 function or other impairments in 5-HT homeostasis. Thus, slow-release 5-HTP could display a wider efficacy because the 5-HTP slow-release principle is not limited by endogenous 5-HT production.

The foregoing is illustrative of the present invention, and is not to be construed as limiting thereof. The invention is defined by the following claims, with equivalents of the claims to be included therein.

That which is claimed is:

1. A method of treating a subject for a psychiatric disorder, wherein said subject has been treated with a serotonin enhancer for at least two weeks, comprising administering to said subject a sustained release formulation of 5-hydroxytryptophan (5-HTP) in combination with said serotonin enhancer,
    wherein said sustained release formulation of 5-HTP is administered in a manner that maintains a substantially constant plasma level of 5-HTP in said subject during said treatment at steady state, and
    wherein said 5-HTP is administered in an amount effective to enhance the effects of the serotonin enhancer,
    to thereby treat the psychiatric disorder.

2. The method of claim 1, wherein said 5-HTP is provided in an amount effective to increase extracellular levels of serotonin in the brain as compared to the levels upon serotonin enhancer treatment without the 5-HTP administration.

3. The method of claim 1, wherein said serotonin enhancer is selected from the group consisting of serotonin reuptake inhibitors, monoamine oxidase inhibitors, tricyclic antidepressants, serotonin agonists, amphetamines, serotonin precursors, serotonin prodrugs, intermediates in the biosynthesis of serotonin, and pharmaceutically acceptable salts thereof.

4. The method of claim 1, wherein said serotonin enhancer is a selective serotonin reuptake inhibitor (SSRI).

5. The method of claim 1, wherein said serotonin enhancer is selected from the group consisting of: citalopram, dapoxetine, escitalopram, fluoxetine, fluvoxamine, indalpine, paroxetine, sertraline, vilazodone, zimelidine and combinations thereof.

6. The method of claim 1, wherein said serotonin enhancer comprises fluoxetine.

7. The method of claim 1 in which said 5-HTP is administered such that the Tmax of said 5-HTP occurs between 4 hours and 8 hours after said administering step.

8. The method of claim 1, wherein said disorder is depression, anxiety, suicidality, obsessive compulsive disorder, or ADHD.

9. The method of claim 8, wherein said disorder is depression.

10. The method of claim 8, wherein said disorder is major depressive disorder.

11. The method of claim 8, wherein said disorder is treatment-resistant depression.

12. The method of claim 1, wherein said subject has a tryptophan hydroxylase 2 (Tph2) variant and/or low endogenous serotonin in the brain.

13. The method of claim 1, wherein said subject has not been determined to have low endogenous serotonin in the brain.

14. The method of claim 1, wherein said administering is subject to the proviso that the subject is not concurrently administered a peripheral decarboxylase inhibitor in an amount effective to reduce peripheral degradation of said 5-HTP.

15. The method of claim 1, wherein said 5-HTP is administered at a rate of from 0.2 to 8 grams per day.

16. The method of claim 1 in which said 5-HTP is administered such that the Tmax of said 5-HTP occurs between 6 hours and 12 hours after said administering step.

17. The method of claim 1 in which said 5-HTP is administered such that the Tmax of said 5-HTP occurs between 4 hours and 12 hours after said administering step.

18. The method of claim 1 in which said 5-HTP is administered such that the Tmax of said 5-HTP occurs between 8 hours and 12 hours after said administering step.

19. The method of claim 1, wherein said 5-HTP is provided at a rate of from 1 to 5 grams per day.

20. The method of claim 1, wherein said administering step is carried out by oral administration.

21. The method of claim 1, wherein said sustained release formulation maintains a plasma 5-HTP level averaging about 100-1000 ng/ml.

22. The method of claim 20, wherein said sustained release formulation of 5-HTP comprises a gastro-retentive formulation.

23. The method of claim 22, wherein said gastro-retentive formulation is a buoyant system, high density system, magnetic system, mucoadhesive system, swelling/expanding system, superporous hydrogel system, or a system with gastric motility retarding agents.

24. The method of claim 22, wherein said gastro-retentive formulation is a buoyant system.

25. The method of claim 22, wherein said gastro-retentive formulation is a swelling/expanding system.

26. The method of claim 20, wherein said sustained release formulation of 5-HTP comprises an oral hydrophilic or lipophilic matrix tablet.

27. The method of claim 26, wherein said oral hydrophilic or lipophilic matrix tablet comprises an oral osmotic system.

28. The method of claim 27, wherein said oral osmotic system comprises an asymmetric membrane technology.

29. The method of claim 27, wherein said oral osmotic system comprises a swellable core technology.

30. The method of claim 26, wherein said oral hydrophilic or lipophilic matrix tablet comprises an oral multiparticulate system.

31. The method of claim 20, wherein said serotonin enhancer is a selective serotonin reuptake inhibitor (SSRI).

32. The method of claim 31, wherein said 5-HTP is administered such that the Tmax of said 5-HTP occurs between 4 hours and 12 hours after said administering step.

* * * * *